US009248054B2

(12) United States Patent
Brown et al.

(10) Patent No.: US 9,248,054 B2
(45) Date of Patent: Feb. 2, 2016

(54) METHODS AND APPARATUS FOR MAKING ELASTIC LAMINATES

(71) Applicant: The Procter & Gamble Company, Cincinnati, OH (US)

(72) Inventors: Darrell Ian Brown, Mason, OH (US); John Andrew Strasemeier, Aurora, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/685,844

(22) Filed: Nov. 27, 2012

(65) Prior Publication Data

US 2014/0144579 A1 May 29, 2014

(51) Int. Cl.
| | |
|---|---|
| *B05C 1/06* | (2006.01) |
| *B05C 1/08* | (2006.01) |
| *B05C 1/12* | (2006.01) |
| *A61F 13/15* | (2006.01) |
| *B05C 5/02* | (2006.01) |
| *B05C 11/10* | (2006.01) |
| *B32B 5/02* | (2006.01) |
| *B32B 5/26* | (2006.01) |

(Continued)

(52) U.S. Cl.
CPC ..... *A61F 13/15699* (2013.01); *A61F 13/15593* (2013.01); *B05C 5/0254* (2013.01); *B05C 11/1034* (2013.01); *B32B 3/266* (2013.01); *B32B 5/022* (2013.01); *B32B 5/024* (2013.01); *B32B 5/26* (2013.01); *B32B 7/12* (2013.01); *B05C 1/0808* (2013.01); *B05C 3/00* (2013.01); *B05C 9/08* (2013.01); *B32B 2262/0253* (2013.01); *B32B 2262/0276* (2013.01); *B32B 2262/062* (2013.01); *B32B 2307/51* (2013.01); *B32B 2307/726* (2013.01); *B32B 2555/00* (2013.01); *Y10T 156/1051* (2015.01)

(58) Field of Classification Search
USPC ......................................... 156/227
See application file for complete search history.

(56) References Cited

U.S. PATENT DOCUMENTS

| | | | |
|---|---|---|---|
| 2,531,036 | A | 7/1946 | Goettsch |
| 3,860,003 | A | 1/1975 | Buell |

(Continued)

FOREIGN PATENT DOCUMENTS

| | | |
|---|---|---|
| CN | 201 088 947 | 7/2008 |
| DE | 88 02 807 U1 | 6/1988 |

(Continued)

OTHER PUBLICATIONS

PCT International Search Report, PCT/US2013/069383 dated Mar. 13, 2014, 12 pages.

(Continued)

*Primary Examiner* — Christopher Schatz
*Assistant Examiner* — Marta Dulko
(74) *Attorney, Agent, or Firm* — Charles R. Matson

(57) ABSTRACT

Aspects of methods and apparatuses herein relate to making elastic laminates, and more particularly, methods and apparatuses for applying fluids onto elastic material positioned on an advancing substrate. The elastic material may be in various forms, such as for example, elastic strands, ribbons, and/or panels. Particular embodiments of the apparatuses and methods disclosed herein provide for the application of viscous fluids, such as adhesives, in pre-determined patterns to elastic material positioned on an advancing substrate.

20 Claims, 29 Drawing Sheets

(51) Int. Cl.
  B32B 7/12 (2006.01)
  B32B 3/26 (2006.01)
  B05C 3/00 (2006.01)
  B05C 9/08 (2006.01)

(56) References Cited

U.S. PATENT DOCUMENTS

| | | |
|---|---|---|
| 4,022,211 A | 5/1977 | Timmons et al. |
| 4,082,059 A | 4/1978 | McIntyre et al. |
| 4,133,774 A | 1/1979 | Brynko et al. |
| 4,135,024 A | 1/1979 | Callahan et al. |
| 4,167,914 A * | 9/1979 | Mladota ............... 118/33 |
| 4,277,301 A | 7/1981 | McIntyre et al. |
| 4,357,370 A | 11/1982 | Alheid |
| 4,481,068 A | 11/1984 | Richey |
| 4,610,678 A | 9/1986 | Weisman et al. |
| 4,673,402 A | 6/1987 | Weisman et al. |
| 4,695,278 A | 9/1987 | Lawson |
| 4,704,115 A | 11/1987 | Buell |
| 4,748,044 A | 5/1988 | Fottinger et al. |
| 4,795,454 A | 1/1989 | Dragoo |
| 4,834,735 A | 5/1989 | Alemany et al. |
| 4,876,982 A | 10/1989 | Claassen |
| 4,888,231 A | 12/1989 | Angstadt |
| 4,909,803 A | 3/1990 | Aziz et al. |
| 4,917,696 A | 4/1990 | DeJonckheere |
| 4,943,451 A | 7/1990 | Zimmer |
| 5,168,806 A | 12/1992 | Reder et al. |
| 5,286,543 A | 2/1994 | Ungpiyakul et al. |
| 5,359,525 A | 10/1994 | Weyenberg |
| 5,500,075 A | 3/1996 | Herrmann |
| 5,525,175 A | 6/1996 | Blenke et al. |
| 5,538,754 A | 7/1996 | Sandock |
| 5,562,646 A | 10/1996 | Goldman et al. |
| 5,599,335 A | 2/1997 | Goldman et al. |
| 5,624,775 A | 4/1997 | Carre et al. |
| 5,628,097 A | 5/1997 | Benson et al. |
| 5,654,040 A | 8/1997 | Matsunaga |
| 5,669,894 A | 9/1997 | Goldman et al. |
| 5,759,274 A | 6/1998 | Maler et al. |
| 5,792,262 A | 8/1998 | Bohn et al. |
| 5,827,609 A | 10/1998 | Ercillo et al. |
| 5,916,661 A | 6/1999 | Benson et al. |
| 6,003,513 A | 12/1999 | Readey et al. |
| 6,033,513 A | 3/2000 | Nakamura |
| 6,074,480 A | 6/2000 | Kakuta |
| 6,107,539 A | 8/2000 | Palumbo et al. |
| 6,193,918 B1 | 2/2001 | McGuire et al. |
| 6,217,690 B1 | 4/2001 | Rajala et al. |
| 6,284,081 B1 | 9/2001 | Vogt et al. |
| 6,287,409 B1 | 9/2001 | Stephany |
| 6,297,424 B1 | 10/2001 | Olson et al. |
| 6,426,119 B1 | 7/2002 | Yapel et al. |
| 6,432,242 B1 | 8/2002 | Nielsen et al. |
| 6,524,660 B2 | 2/2003 | Quiel et al. |
| 6,531,027 B1 | 3/2003 | Lender et al. |
| 6,545,197 B1 | 4/2003 | Muller et al. |
| 6,569,275 B1 | 5/2003 | Popp et al. |
| 6,582,543 B1 * | 6/2003 | Nilsson et al. ............ 156/216 |
| 6,585,841 B1 | 7/2003 | Popp et al. |
| 6,602,454 B2 | 8/2003 | McGuire et al. |
| 6,699,347 B2 | 3/2004 | Lehrter et al. |
| 6,790,798 B1 | 9/2004 | Suzuki et al. |
| 6,801,828 B2 | 10/2004 | Popp et al. |
| 6,808,582 B2 | 10/2004 | Popp et al. |
| 6,820,022 B2 | 11/2004 | Popp et al. |
| 6,881,471 B2 | 4/2005 | Toussant et al. |
| 6,942,894 B2 | 9/2005 | Alberg et al. |
| 7,045,031 B2 | 5/2006 | Popp et al. |
| 7,056,386 B2 | 6/2006 | Pahl |
| 7,097,725 B2 | 8/2006 | Yoneoka et al. |
| 7,123,981 B2 | 10/2006 | Dollevoet et al. |
| 7,163,740 B2 | 1/2007 | Rosati et al. |
| 7,252,855 B2 | 8/2007 | Haskett et al. |
| 7,432,413 B2 | 10/2008 | Roe et al. |
| 7,444,932 B2 | 11/2008 | Strand et al. |
| 7,460,250 B2 | 12/2008 | Keightley et al. |
| 7,489,410 B2 | 2/2009 | Nishio |
| 7,569,039 B2 | 8/2009 | Matsuda et al. |
| 7,611,582 B2 | 11/2009 | McNeil et al. |
| 7,625,605 B2 | 12/2009 | Cooprider et al. |
| 7,667,857 B2 | 2/2010 | Nishio |
| 7,736,456 B2 | 6/2010 | Branca et al. |
| 7,752,995 B2 | 7/2010 | Tremblay et al. |
| 8,145,343 B2 | 3/2012 | DeBruler et al. |
| 8,145,344 B2 | 3/2012 | DeBruler et al. |
| 8,163,332 B2 | 4/2012 | Emoto et al. |
| 8,186,296 B2 * | 5/2012 | Brown et al. ............... 118/261 |
| 8,244,393 B2 | 8/2012 | McLaughlin et al. |
| 8,445,067 B2 | 5/2013 | Suzuki et al. |
| 8,574,668 B2 * | 11/2013 | Brown et al. ............ 427/208.2 |
| 2001/0053898 A1 | 12/2001 | Olson et al. |
| 2002/0007162 A1 | 1/2002 | Cammarota et al. |
| 2003/0138570 A1 | 7/2003 | Kaylor et al. |
| 2004/0091701 A1 | 5/2004 | Toussant et al. |
| 2004/0097895 A1 | 5/2004 | Busam et al. |
| 2004/0102125 A1 | 5/2004 | Morman et al. |
| 2004/0158212 A1 | 8/2004 | Ponomarenko et al. |
| 2005/0087292 A1 * | 4/2005 | McFall et al. ............... 156/290 |
| 2005/0107764 A1 | 5/2005 | Matsuda et al. |
| 2005/0233072 A1 | 10/2005 | Stephan et al. |
| 2006/0021695 A1 | 2/2006 | Blessing et al. |
| 2006/0048880 A1 | 3/2006 | Blessing et al. |
| 2007/0003736 A1 | 1/2007 | Saarvali et al. |
| 2007/0065574 A1 | 3/2007 | Rosati et al. |
| 2007/0142798 A1 | 6/2007 | Goodlander et al. |
| 2007/0219521 A1 | 9/2007 | Hird et al. |
| 2007/0287983 A1 | 12/2007 | Lodge et al. |
| 2008/0114319 A1 * | 5/2008 | Burns et al. ............ 604/385.01 |
| 2008/0132865 A1 | 6/2008 | Li et al. |
| 2008/0215166 A1 | 9/2008 | Blessing et al. |
| 2008/0221543 A1 | 9/2008 | Wilkes et al. |
| 2008/0245298 A1 | 10/2008 | Ayers |
| 2009/0312730 A1 | 12/2009 | LaVon et al. |
| 2010/0051166 A1 | 3/2010 | Hundorf et al. |
| 2010/0078127 A1 | 4/2010 | Yamamoto et al. |
| 2010/0193138 A1 | 8/2010 | Eckstein et al. |
| 2010/0230056 A1 | 9/2010 | Aono |
| 2010/0252178 A1 * | 10/2010 | Takino et al. ............... 156/164 |
| 2010/0264369 A1 | 10/2010 | Zhang |
| 2011/0036487 A1 | 2/2011 | Rajala et al. |
| 2011/0137274 A1 | 6/2011 | Klofta et al. |
| 2011/0139657 A1 | 6/2011 | Hird et al. |
| 2011/0139658 A1 | 6/2011 | Hird et al. |
| 2011/0139659 A1 | 6/2011 | Hird et al. |
| 2011/0139662 A1 | 6/2011 | Hird et al. |
| 2011/0152812 A1 | 6/2011 | Hird et al. |
| 2011/0274834 A1 * | 11/2011 | Brown et al. ............ 427/207.1 |
| 2012/0061015 A1 | 3/2012 | Lavon et al. |
| 2012/0061016 A1 | 3/2012 | Lavon et al. |
| 2012/0152441 A1 | 6/2012 | Rajala |
| 2012/0273129 A1 | 11/2012 | Handziak |
| 2012/0316046 A1 | 12/2012 | Jackels et al. |
| 2013/0129925 A1 | 5/2013 | Hanai et al. |
| 2013/0287953 A1 | 10/2013 | McGuire et al. |
| 2014/0057058 A1 | 2/2014 | Yapel et al. |

FOREIGN PATENT DOCUMENTS

| | | |
|---|---|---|
| DE | 10 2006 040 702 | 3/2008 |
| DE | 10 2011 076 748 | 12/2011 |
| EP | 2 191 959 A1 | 0/2010 |
| EP | 0 372 120 A2 | 6/1990 |
| EP | 0 380 781 A2 | 8/1990 |
| EP | 0 535 579 A2 | 9/1990 |
| EP | 0 730 914 A2 | 1/1996 |
| EP | 0 745 368 A1 | 12/1996 |
| EP | 0 788 408 B1 | 11/2001 |
| EP | 1 621 166 A2 | 1/2006 |
| EP | 1 863 594 B1 | 1/2011 |
| EP | 2 420 325 A2 | 2/2012 |
| EP | 2 520 426 A1 | 11/2012 |
| FR | 2 873 382 A1 | 6/2008 |
| JP | 2007-143676 | 6/2007 |

(56) References Cited

FOREIGN PATENT DOCUMENTS

| | | |
|---|---|---|
| JP | 2009-233506 | 10/2009 |
| KR | 2009-0101705 A1 | 9/2009 |
| WO | WO 96/04874 A1 | 2/1996 |
| WO | WO 00/76438 A2 | 12/2000 |
| WO | WO 00/76443 A1 | 12/2000 |
| WO | WO 2005/014263 | 2/2005 |
| WO | WO 2006/098934 A1 | 9/2006 |
| WO | WO 2008/038563 | 4/2008 |
| WO | WO 2012/026330 | 3/2012 |

OTHER PUBLICATIONS

U.S. Appl. No, 13/685,948, filed on Nov. 27, 2012—Office Action mailed. Feb. 4, 2013 (11 pages).

U.S. Appl. No. 13/685,817, filed Nov. 27, 2012—Notice of Allowance mailed Nov. 5, 2014 (7 pages).

U.S. Appl. No. 13/685,817, filed Nov. 27, 2012—Office Action mailed Nov. 14, 2013 (9 pages).

U.S. Appl. No. 13/685,817, filed Nov. 27, 2012—Office Action mailed Jul. 8, 2013 (9 pages).

U.S. Appl. No. 13/685,948, filed Nov. 27, 2012—Office Action mailed Jul. 15, 2013 (10 pages).

U.S. Appl. No. 13/685,948, filed Nov. 27, 2012—Office Action mailed Feb. 12, 2014 (12 pages).

U.S. Appl. No. 13/685,959, filed Nov. 27, 2012—Office Action mailed Jan. 13, 2015, (9 pages).

U.S. Appl. No. 13/685,817, filed Nov. 27, 2012—Notice of Allowance mailed May 29, 2015 (6 pages).

U.S. Appl. No. 13/685,948, filed Nov. 27, 2012 —Office Action mailed May 21, 2015 (11 pages).

U.S. Appl. No. 13/685,959, filed Nov. 27, 2012 —Office Action mailed Jul. 23, 2015, (11 pages).

* cited by examiner

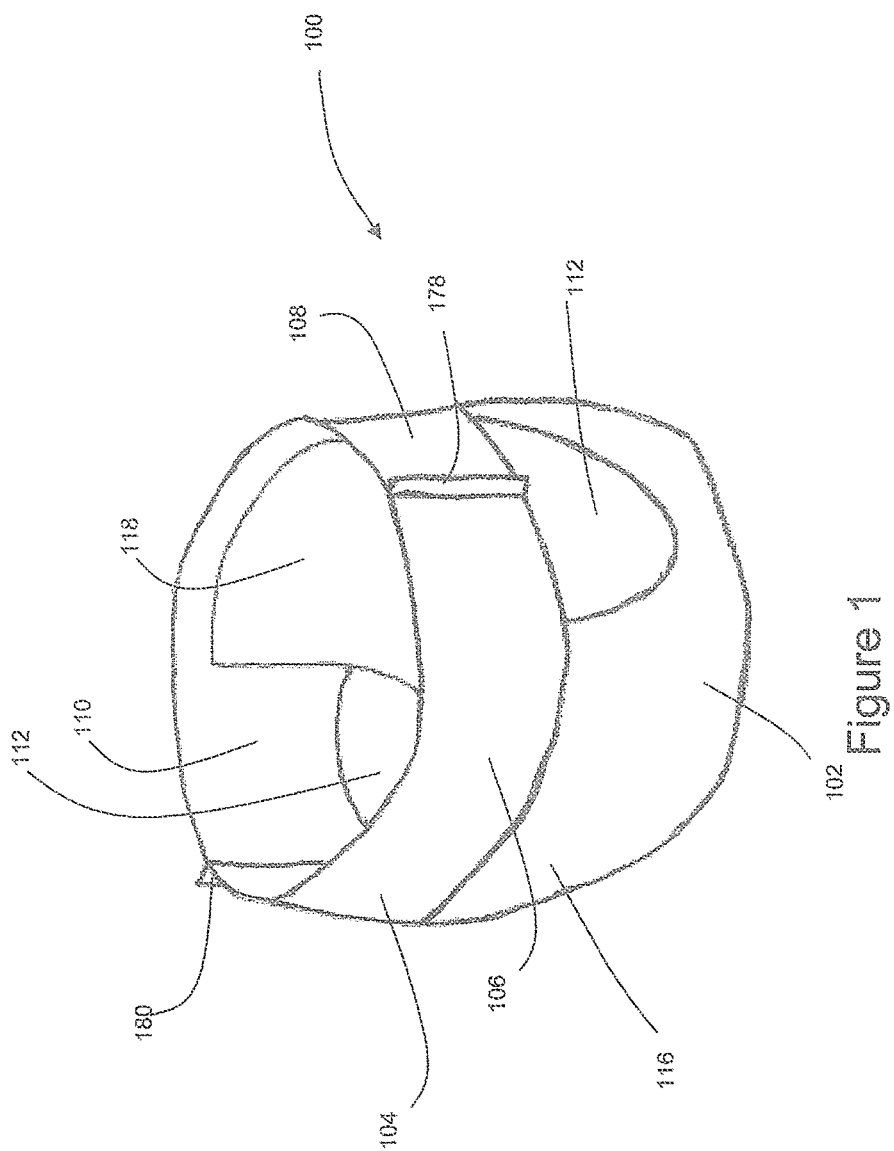

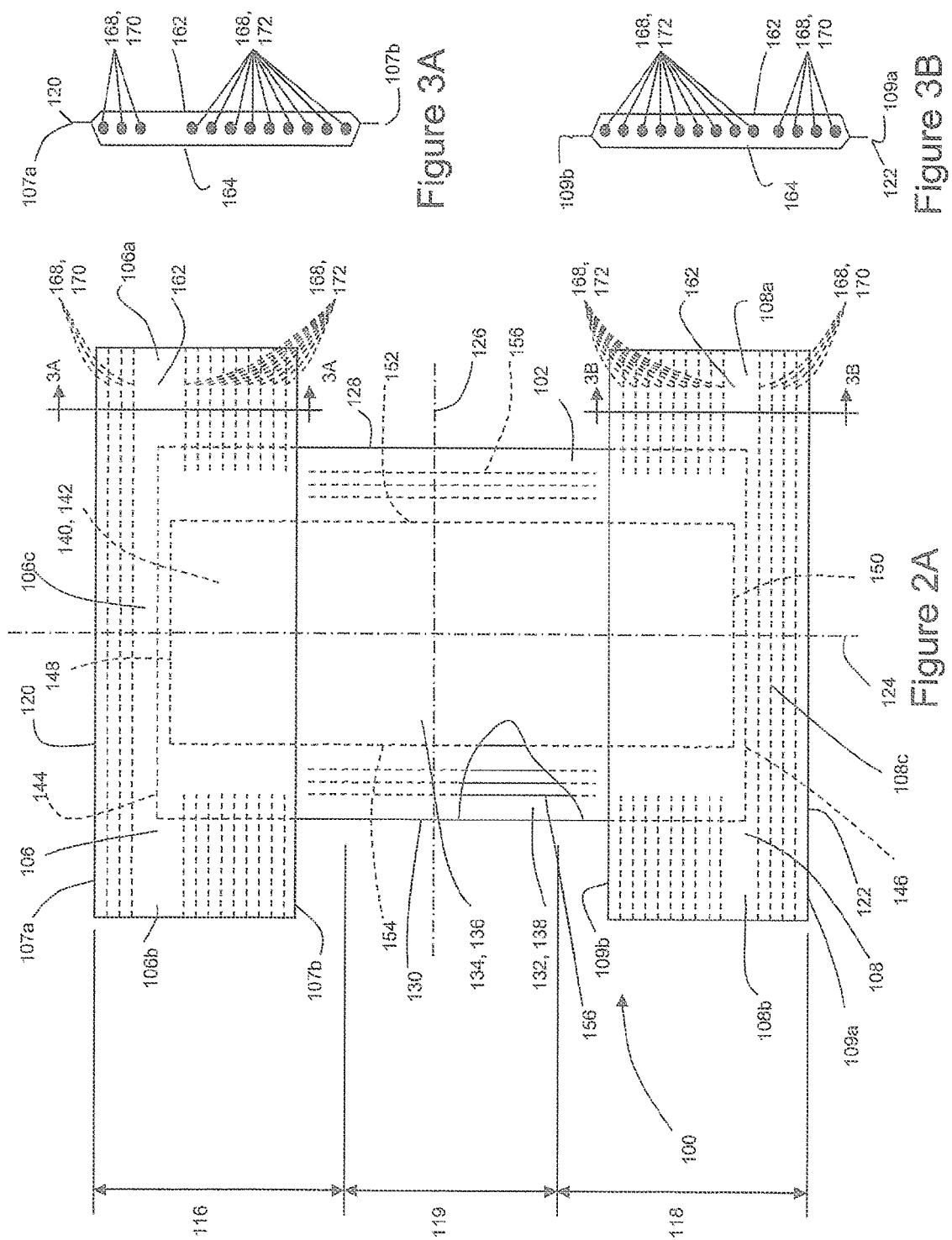

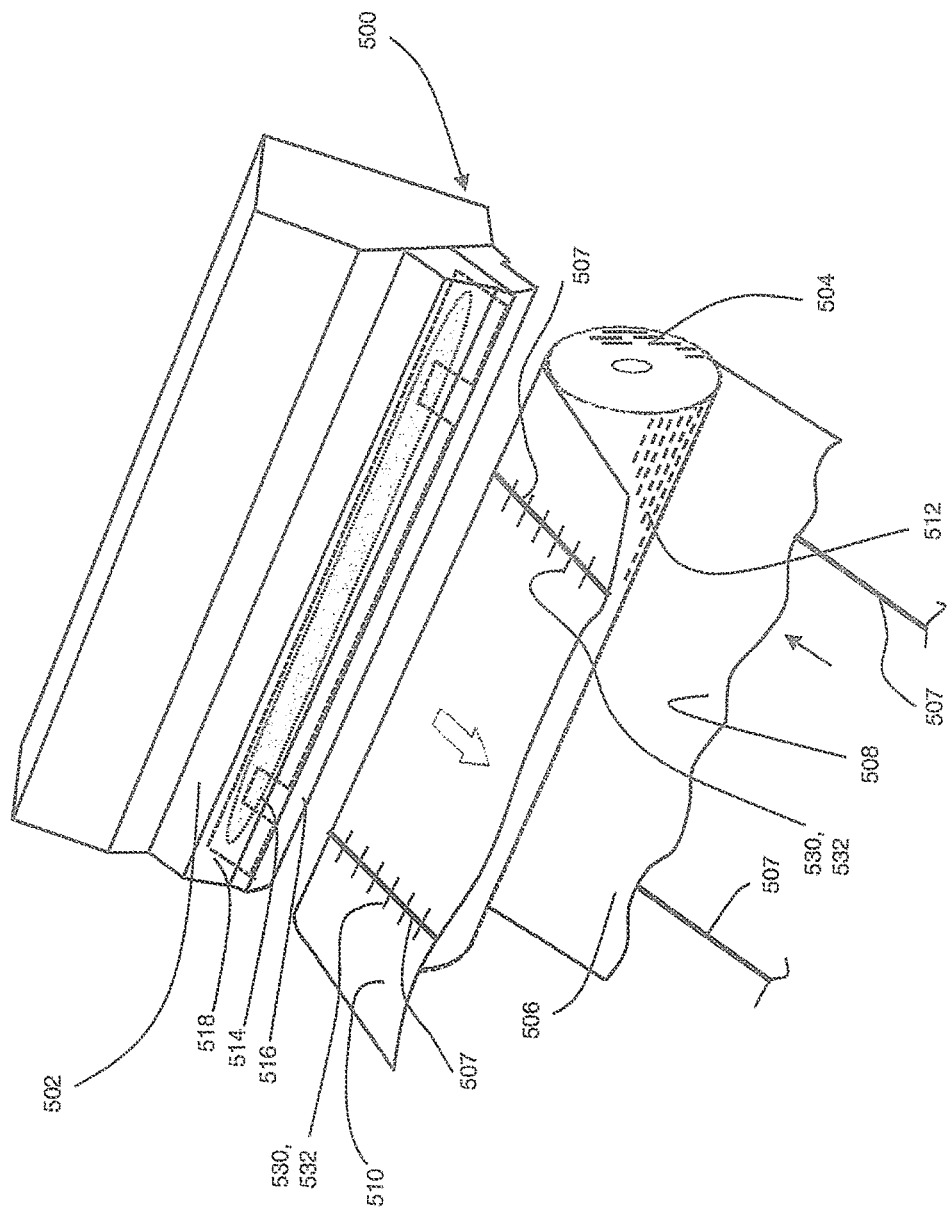

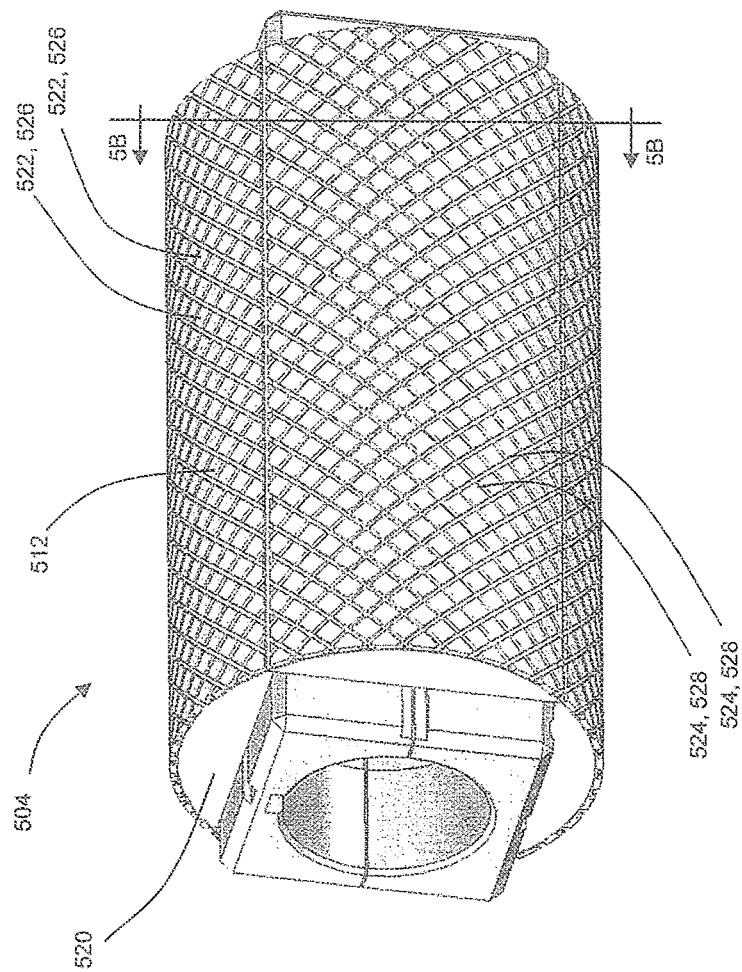

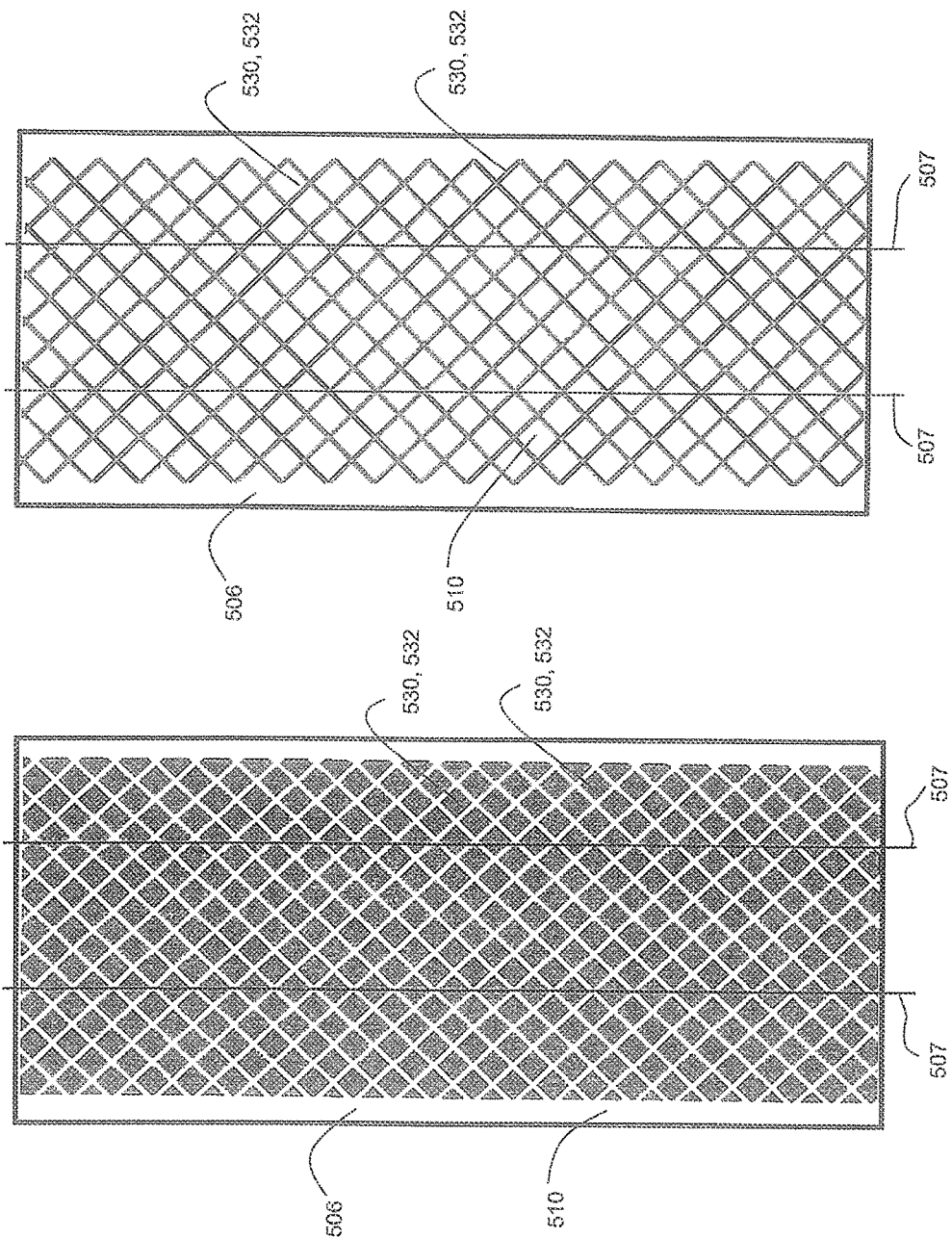

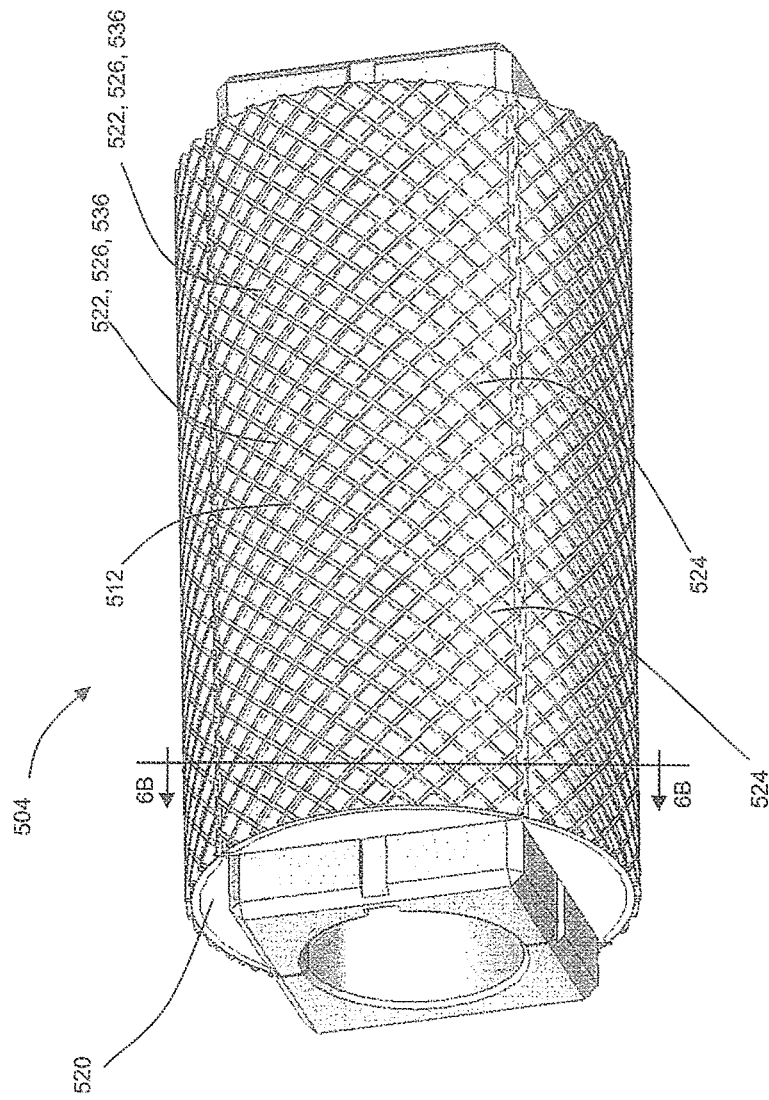

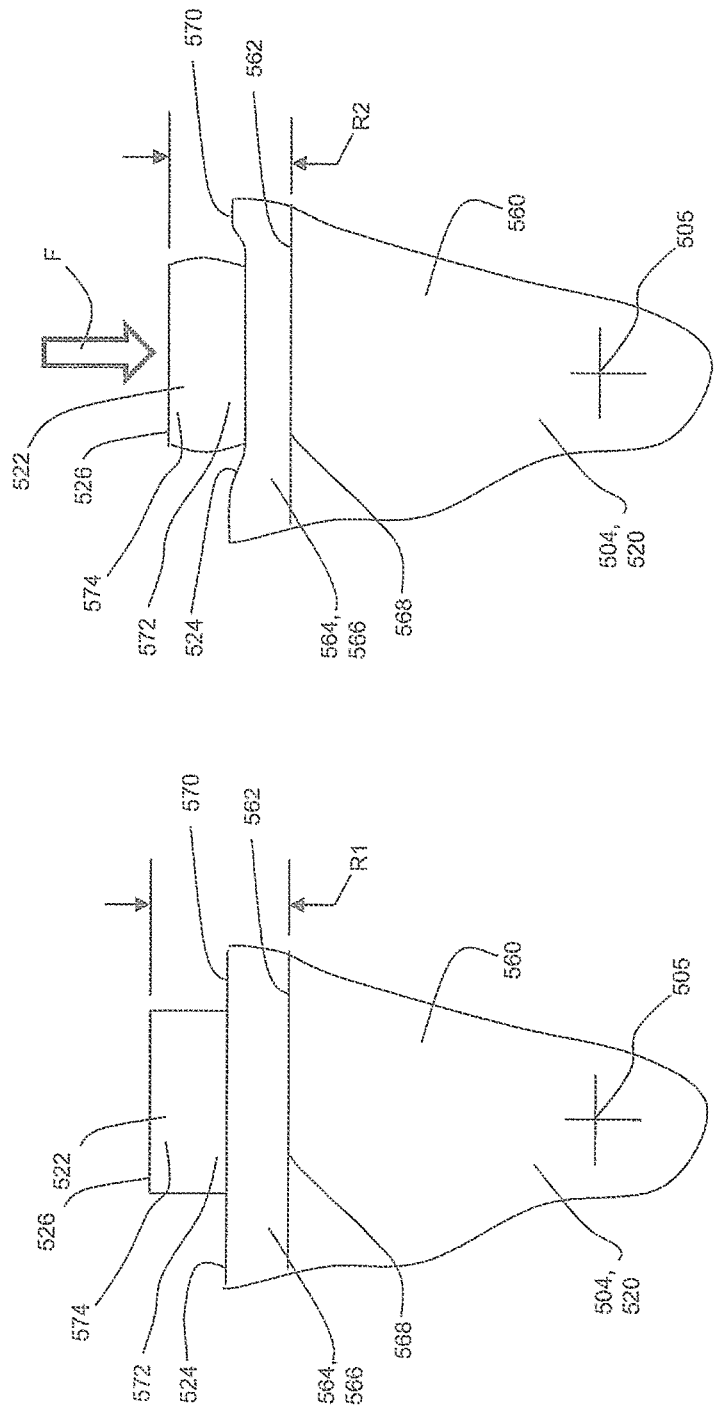

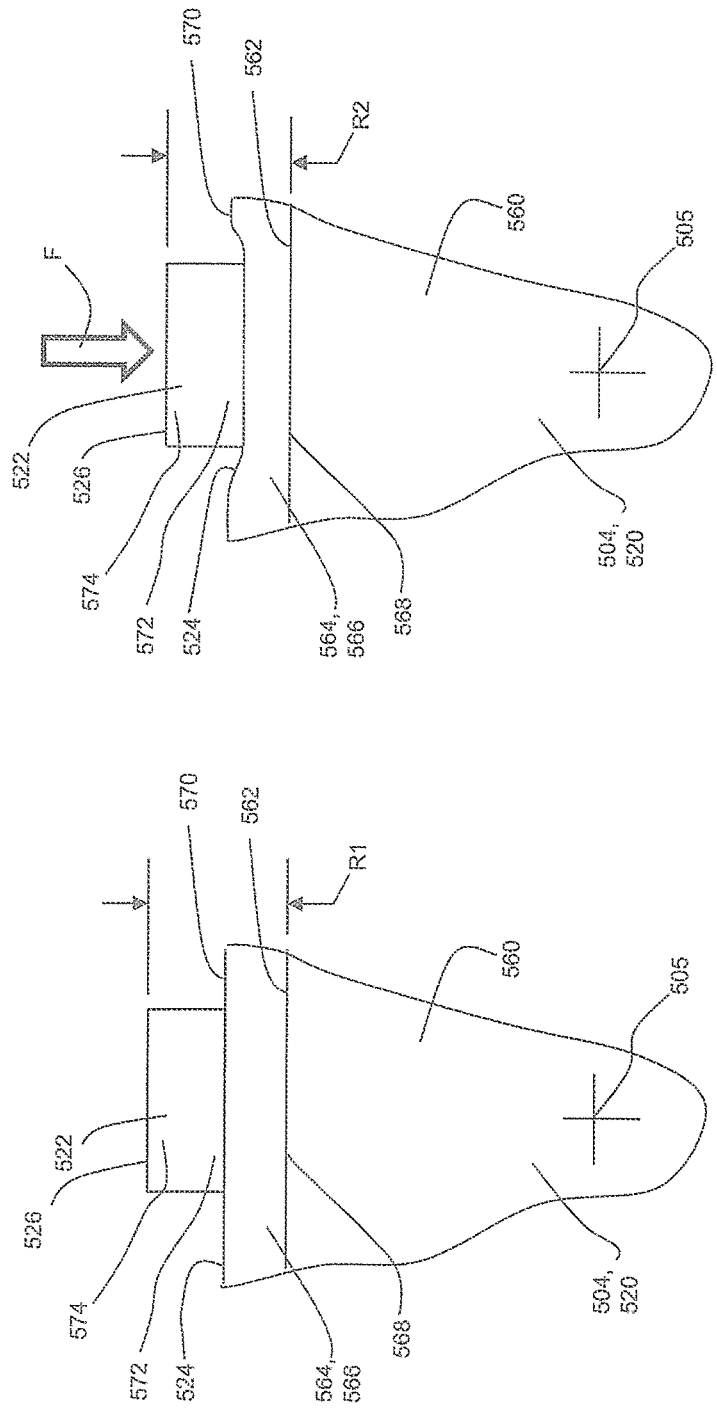

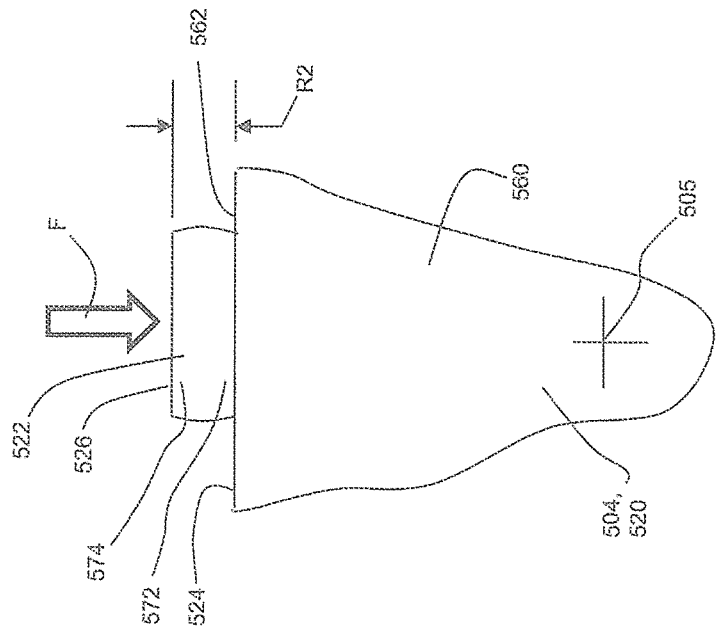
Figure 7C2
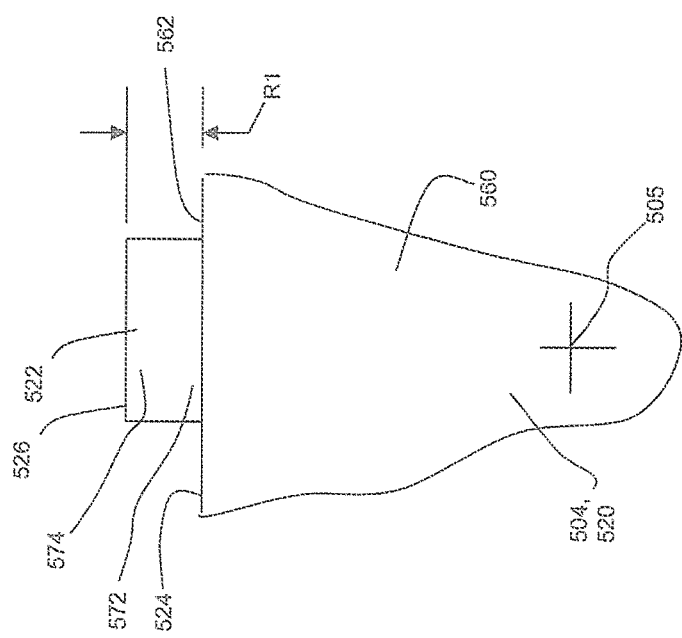
Figure 7C1

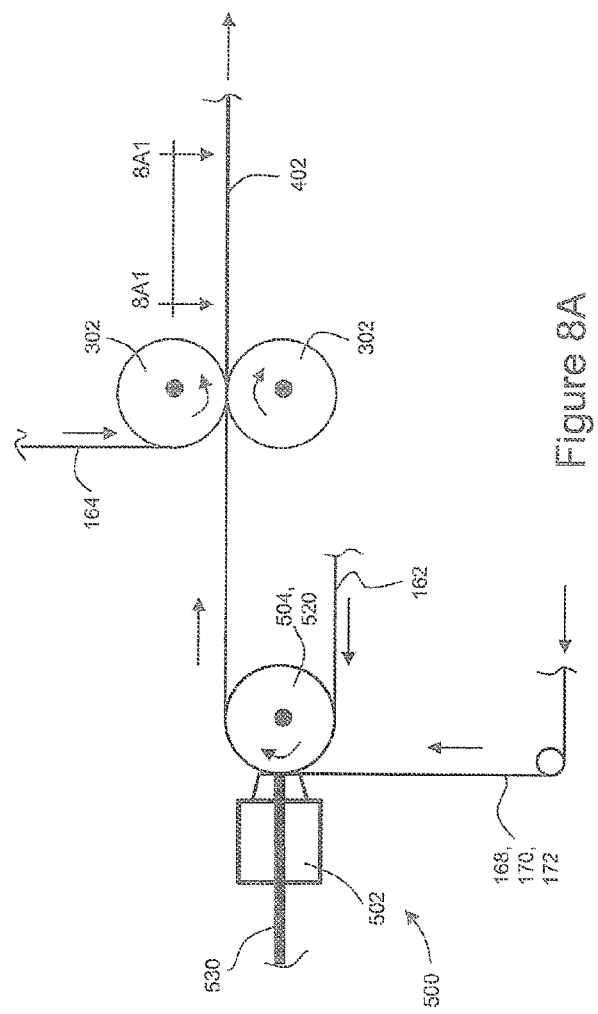
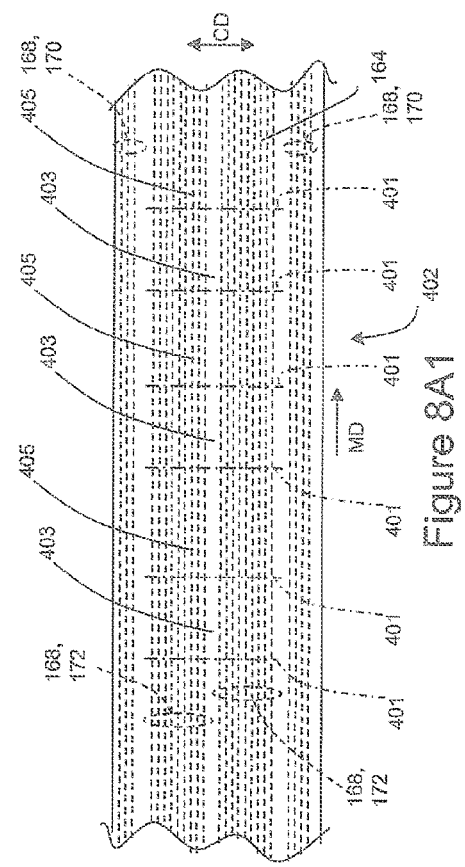
Figure 8A
Figure 8A1

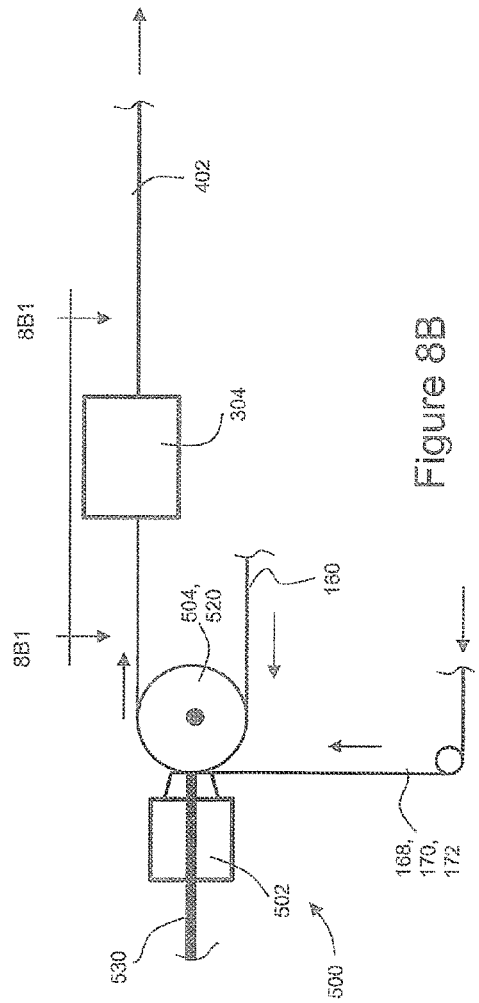
Figure 8B
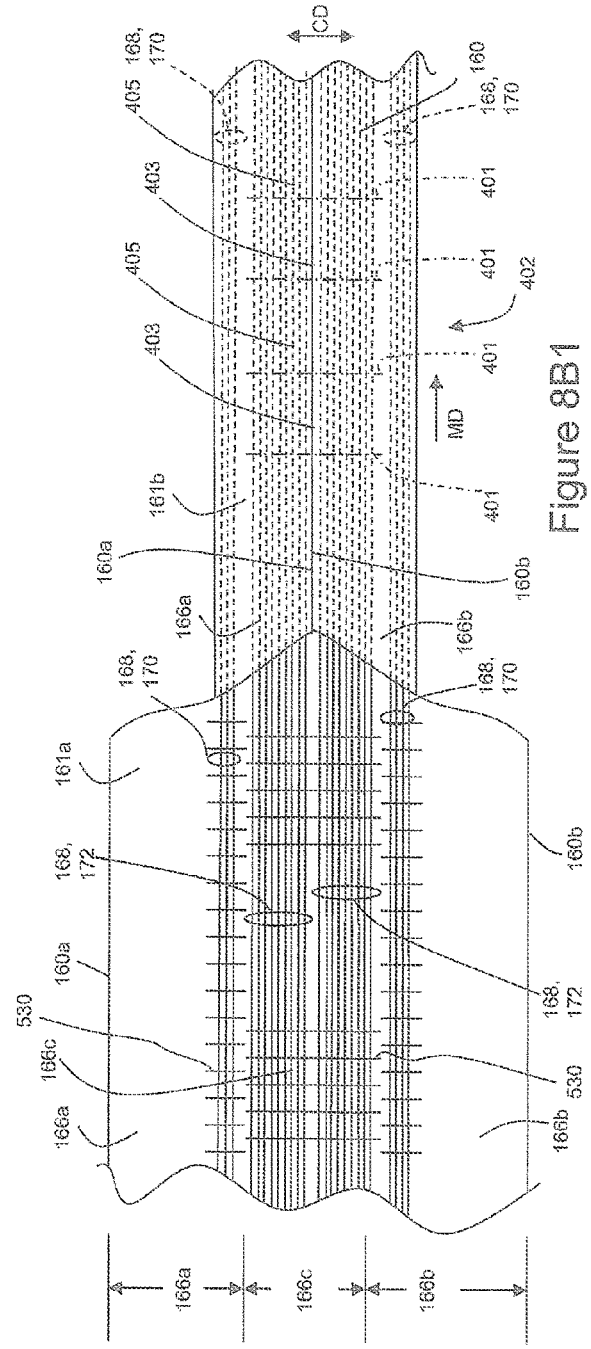
Figure 8B1

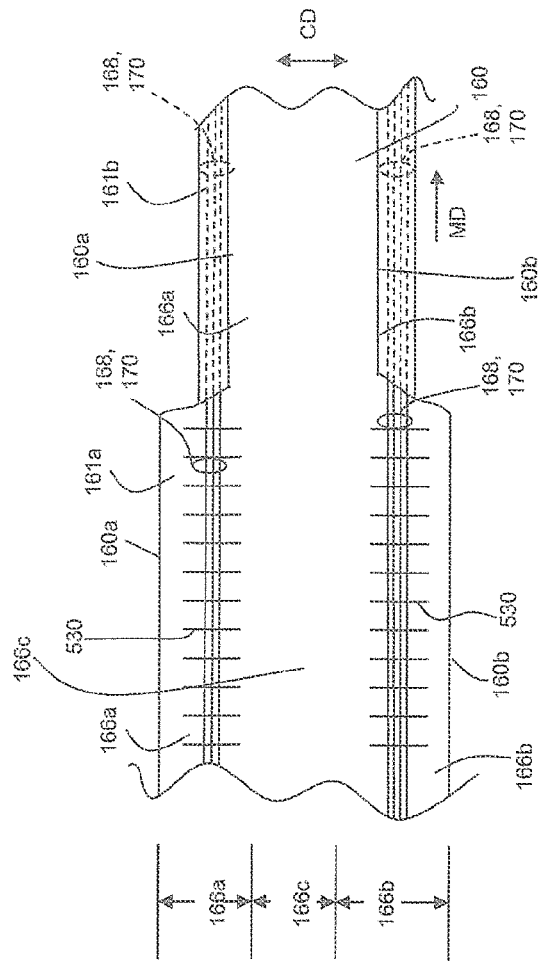
Figure 8C1
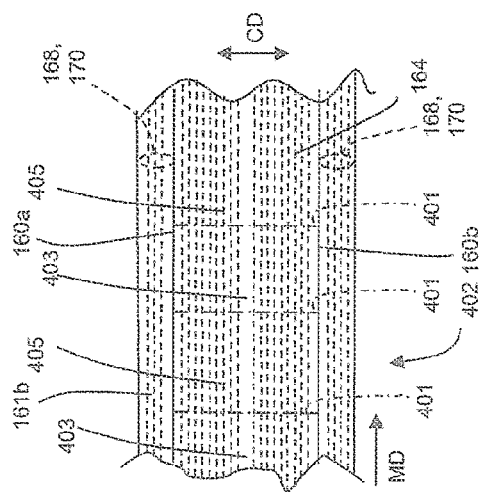
Figure 8C2

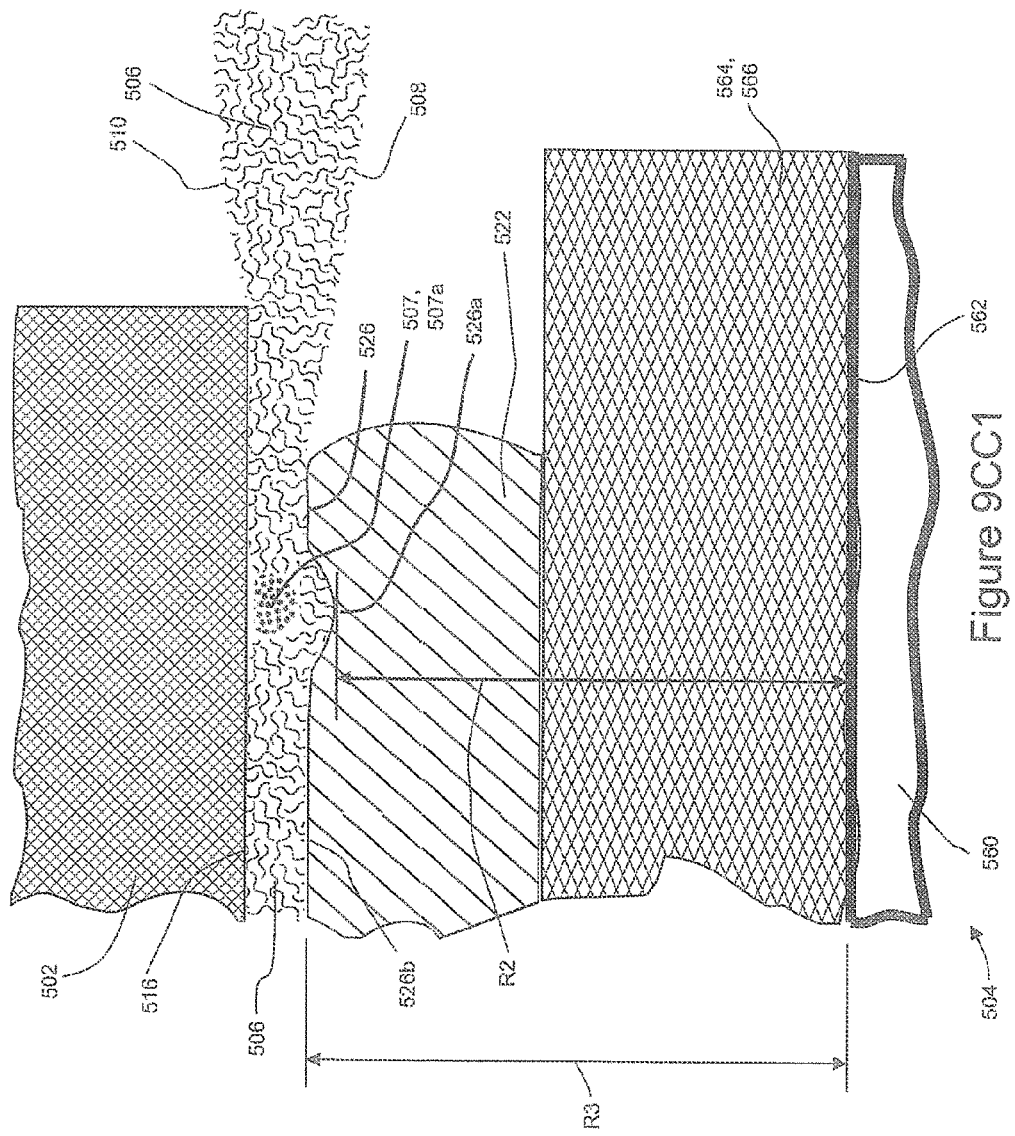
Figure 9CC1

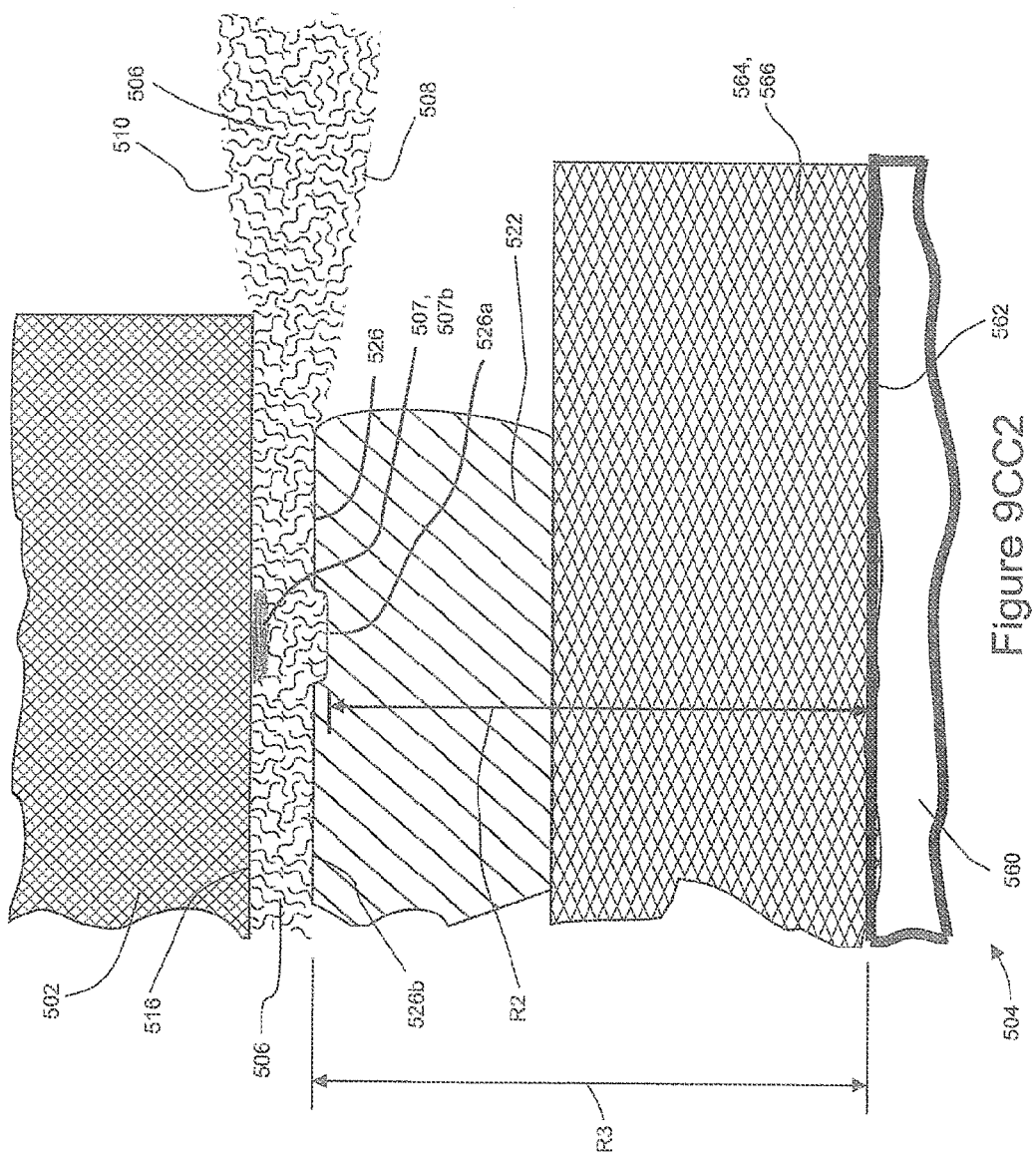

METHODS AND APPARATUS FOR MAKING ELASTIC LAMINATES

FIELD OF THE INVENTION

The present disclosure relates to methods for manufacturing absorbent articles, and more particularly, to apparatuses and methods for making elastic laminates for absorbent articles.

BACKGROUND OF THE INVENTION

Along an assembly line, various types of articles, such as for example, diapers and other absorbent articles, may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

Various methods and apparatuses may be used for attaching different components to the advancing web and/or otherwise modify the advancing web. For example, some production operations are configured to apply relatively high viscosity fluids, such as hot melt adhesives, to elastic strands to be combined with an advancing web to create an elastic laminate. In some instances, the production operations are configured to apply hot melt adhesives to advancing elastic strands and/or a web in pre-determined patterns. These operations may include the use of systems and methods such as slot die coating, direct gravure, offset gravure and reverse gravure roll coating processes that are extensively described in the art. However, current systems and methods for applying adhesives to an advancing substrate and/or elastic strands may have certain limitations.

For example, some manufacturing processes of absorbent articles such as feminine hygiene pads, baby diapers, and adult incontinence pads use electro-pneumatic switching valves to intermittently transfer adhesive to advancing elastic strands and/or substrates. However, the quality and precision of intermittent transfer of fluids to advancing elastics and/or substrates may be limited by the speed of the on/off cycle of switching valves used to interrupt the flow of fluid to the adhesive applicator. Thus, as web processing speeds increase, the ability of current adhesive application methods to achieve fine resolution of on/off coat patterns in the direction of web travel decreases. Consequently, it would be beneficial to provide apparatuses and methods that apply adhesives and other fluids to a substrate in patterns with relatively high resolution and high speeds without being limited by the speed of on/off cycling of switching valves used to interrupt the flow of fluid to the slot die of the fluid applicator.

SUMMARY OF THE INVENTION

Aspects of methods and apparatuses herein relate to making elastic laminates, and more particularly, methods and apparatuses for applying fluids onto elastic material positioned on an advancing substrate. The elastic material may be in various forms, such as for example, elastic strands, ribbons, and/or panels. Particular embodiments of the apparatuses and methods disclosed herein provide for the application of viscous fluids, such as adhesives, in pre-determined patterns to elastic material positioned on an advancing substrate.

In one form, a method may be used to apply adhesive discharged from a slot die applicator to a substrate and an elastic material, the slot die applicator including a slot opening, a first lip, and a second lip, the slot opening located between the first lip and the second lip; wherein the substrate has a first surface disposed opposite of a second surface and an unconstrained caliper, Hs, and wherein the elastic material has a maximum thickness, Et. The method includes the steps of: advancing the substrate in a machine direction; advancing the elastic material in the machine direction; positioning the elastic material on the second surface of the substrate; engaging the substrate with a substrate carrier, the substrate carrier comprising: a non-compliant support surface and a pattern element, the pattern element including a pattern surface, the substrate carrier positioned adjacent the slot die applicator to define a minimum distance, Hg, between the pattern surface of the pattern element and the first lip and the second lip of the slot die applicator that is less than the sum of the unconstrained caliper, Hs, of the substrate and the maximum thickness, Et, of the elastic material; advancing the second surface of the substrate and the elastic material past the slot die applicator while the first surface of the substrate is disposed on the substrate carrier; intermittently deflecting a first portion of the pattern surface toward the non-compliant support surface by advancing the substrate and the elastic material between the pattern element and the first lip, the slot opening, and the second lip of the slot die applicator while the first surface of the substrate is disposed on the substrate carrier; and discharging adhesive from the slot opening of the slot die applicator onto the elastic material and the second surface of the substrate.

In another form, a method may be adapted to apply adhesive discharged from a slot die applicator to a substrate and an elastic material, the slot die applicator including a slot opening, a first lip, and a second lip, the slot opening located between the first lip and the second lip of the slot die applicator; wherein the substrate has a first surface disposed opposite of a second surface and an unconstrained caliper, Hs, and wherein the elastic material has a maximum thickness, Et. The method includes the steps of: advancing the substrate in a machine direction; advancing the elastic material in the machine direction; positioning the elastic material on the second surface of the substrate; engaging the substrate with a substrate carrier, the substrate carrier comprising: a pattern element including a pattern surface, the substrate carrier positioned adjacent the slot die applicator to define a minimum distance, Hg, between the pattern surface of the pattern element and the first lip and the second lip that is less than the sum of the unconstrained caliper, Hs, of the substrate and the maximum thickness, Et, of the elastic material; advancing the second surface of the substrate and the elastic material past the slot die applicator while the first surface of the substrate is disposed on the substrate carrier; intermittently deflecting a first portion of the pattern surface away from the slot die applicator by advancing the substrate and the elastic material between the pattern element and the first lip, the slot opening, and the second lip of the slot die applicator while the first surface of the substrate is disposed on the substrate carrier;

and discharging adhesive from the slot opening of the slot die applicator onto the elastic material and the second surface of the substrate.

In yet another form, a method for making an elastic laminate includes the steps of: advancing a substrate, the substrate comprising a first surface disposed opposite of a second surface; positioning the elastic material on the second surface of the substrate; engaging the substrate with a substrate carrier, the substrate carrier comprising: a pattern element including a pattern surface, the substrate carrier positioned adjacent the slot die applicator to define a minimum distance, Hg, between the pattern surface of the pattern element and the first lip and the second lip of the slot die applicator that is less than the sum of the unconstrained caliper, Hs, of the substrate and the maximum thickness, Et, of the elastic material; advancing the second surface of the substrate and the elastic material past the slot die applicator while the first surface of the substrate is disposed on the substrate carrier; intermittently deflecting a first portion of the pattern surface away from the slot die applicator by advancing the substrate and the elastic material between the pattern element and the first lip, the slot opening, and the second lip of the slot die applicator while the first surface of the substrate is disposed on the substrate carrier; and discharging adhesive from the slot opening of the slot die applicator onto the elastic material and the second surface of the substrate.

BRIEF DESCRIPTION OF THE DRAWINGS

FIG. 1 is a perspective view of a diaper pant.

FIG. 2A is a partially cut away plan view of the diaper pant shown in FIG. 1.

FIG. 3A is a cross-sectional view of the diaper pants of FIG. 2A taken along line 3A-3A.

FIG. 3B is a cross-sectional view of the diaper pants of FIG. 2A taken along line 3B-3B.

FIG. 4 is a perspective view of a fluid application apparatus positioned adjacent to an advancing substrate and elastic material.

FIG. 5A is a perspective view of an embodiment of a substrate carrier including a pattern roller having a continuous base surface and a plurality of pattern surfaces.

FIG. 5C is a top side view of a substrate and elastic material showing a first example adhesive pattern thereon.

FIG. 6A is a perspective view of an embodiment of a substrate carrier including a pattern roller having a continuous pattern surface and plurality of base surfaces.

FIG. 6C is a top side view of a substrate showing a second example adhesive pattern thereon.

FIG. 7A1 is a detailed view of the substrate carrier of FIG. 7 including a compliant pattern element and a compliant base layer connected with a base roll.

FIG. 7A2 is a detailed view of the pattern surface of the pattern element from FIG. 7A1 deflected by a force or forces applied to the pattern surface.

FIG. 7B1 is a detailed view of the substrate carrier of FIG. 7 including a non-compliant pattern element and a compliant base layer connected with a base roll.

FIG. 7B2 is a detailed view of the pattern surface of the pattern element from FIG. 7B1 deflected by a force or forces applied to the pattern surface.

FIG. 7C1 is a detailed view of the substrate carrier of FIG. 7 including a compliant pattern element connected with a base roll.

FIG. 7C2 is a detailed view of the pattern surface of the pattern element from FIG. 7C1 deflected by a force or forces applied to the pattern surface.

FIG. 8A is a schematic side view of a first converting configuration for making an elastic laminate.

FIG. 8A1 is a view of a continuous length of an elastic laminate from FIG. 8A taken along line 8A1-8A1.

FIG. 8B is a schematic side view of a second converting configuration for making an elastic laminate.

FIG. 8B1 is a view of a continuous length of an elastic laminate from FIG. 8B taken along line 8B1-8B1.

FIG. 8C1 is a view of a continuous length of an elastic laminate from FIG. 8C taken along line 8C1-8C1.

FIG. 8C2 is a view of a continuous length of an elastic laminate from FIG. 8C taken along line 8C2-8C2.

FIG. 9CC1 is a cross-sectional view of the substrate carrier and fluid application device showing an elastic strand and substrate taken along the line CC-CC in FIG. 9C.

FIG. 9CC2 is a cross-sectional view of the substrate carrier and fluid application device showing an elastic film and substrate taken along the line CC-CC in FIG. 9C.

DETAILED DESCRIPTION OF THE INVENTION

Figure 4A:
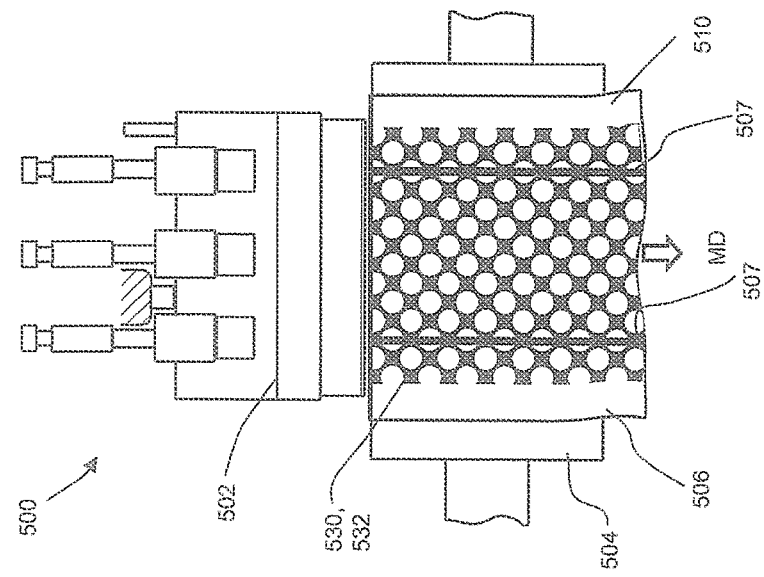
FIG. 4A is a front side view of a fluid application apparatus depositing fluid onto an advancing substrate and elastic material in a first example pattern.
Figure 4B:
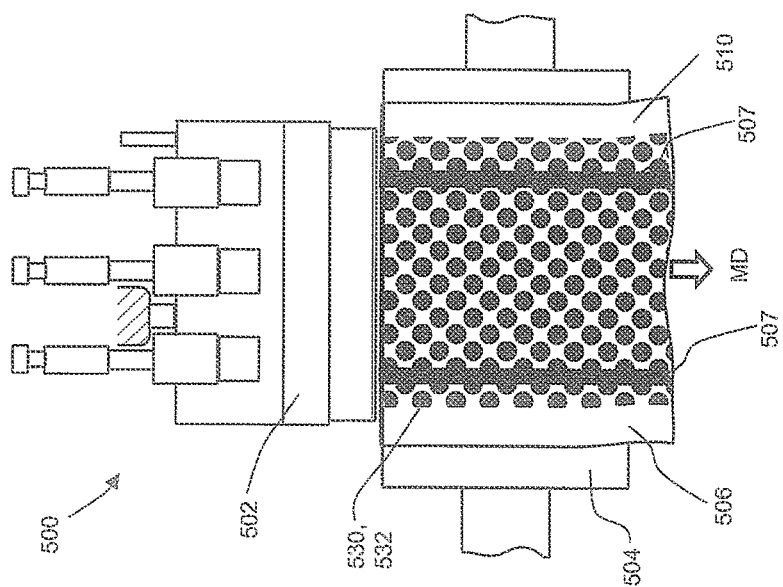
FIG. 4B is a front side view of a fluid application apparatus depositing fluid onto an advancing substrate and elastic material in a second example pattern.
Figure 4D:
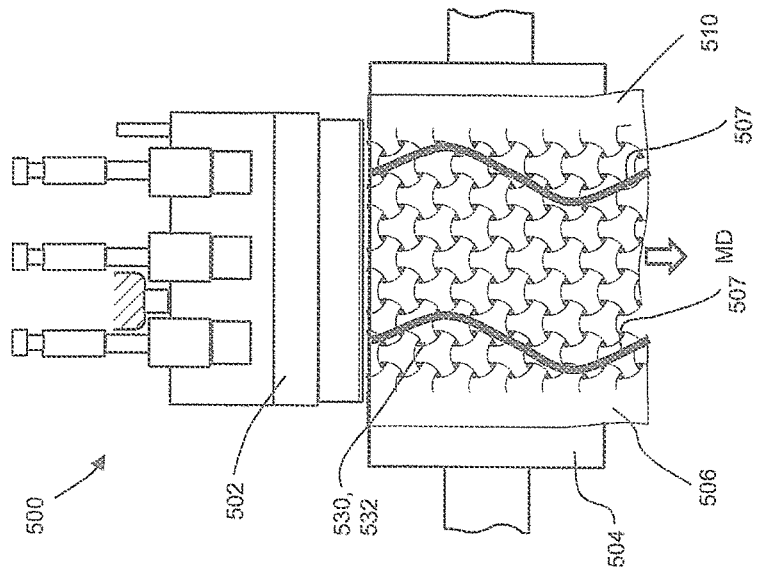
FIG. 4D is a front side view of a fluid application apparatus depositing fluid onto an advancing substrate and elastic material in a fourth example pattern.
Figure 4C:
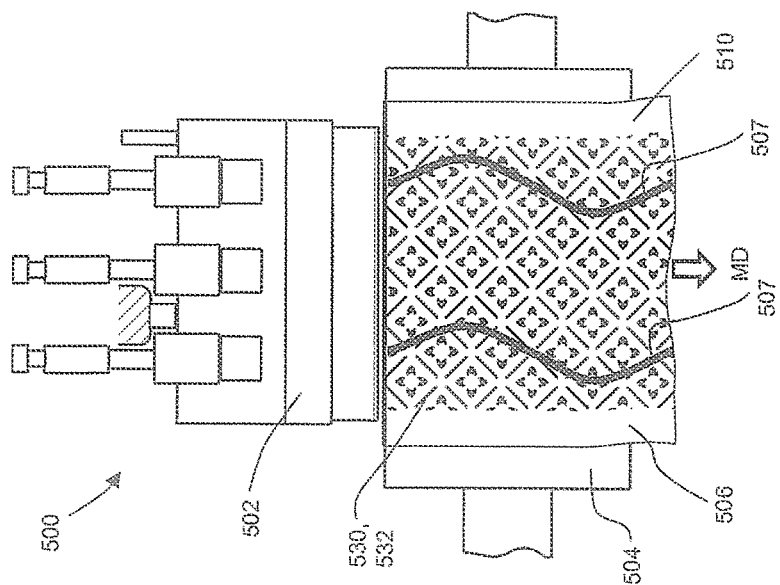
FIG. 4C is a front side view of a fluid application apparatus depositing fluid onto an advancing substrate and elastic material in a third example pattern.

The following term explanations may be useful in understanding the present disclosure:

"Absorbent article" is used herein to refer to consumer products whose primary function is to absorb and retain soils and wastes. Non-limiting examples of absorbent articles include diapers, training pants, pull-on pant-type diapers, refastenable diapers or pant-type diapers, incontinence briefs and undergarments, diaper holders and liners, feminine hygiene garments such as panty liners, absorbent inserts, and the like.

"Diaper" is used herein to refer to an absorbent article generally worn by infants and incontinent persons about the lower torso.

The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "disposed" is used herein to mean that an element(s) is formed (joined and positioned) in a particular place or position as a macro-unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a layer or layers or fibrous materials, films and foils such as plastic films or metallic foils that may be used alone or laminated to one or more web, layer, film and/or foil. As such, a web is a substrate.

The term "nonwoven" refers herein to a material made from continuous (long) filaments (fibers) and/or discontinuous (short) filaments (fibers) by processes such as spunbonding, meltblowing, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The terms "elastic" and "elastomeric" as used herein refer to any material that upon application of a biasing force, can stretch to an elongated length of at least about 110% of its relaxed, original length (i.e. can stretch to 10% more than its original length), without rupture or breakage, and upon release of the applied force, recovers at least about 40% of its elongation. For example, a material that has an initial length of 100 mm can extend at least to 110 mm, and upon removal of the force would retract to a length of 106 mm (40% recovery). The term "inelastic" refers herein to any material that does not fall within the definition of "elastic" above.

The term "extensible" as used herein refers to any material that upon application of a biasing force, can stretch to an elongated length of at least about 110% of its relaxed, original length (i.e. can stretch to 10%), without rupture or breakage, and upon release of the applied force, shows little recovery, less than about 40% of its elongation.

The terms "activating", "activation" or "mechanical activation" refer to the process of making a substrate, or an elastomeric laminate more extensible than it was prior to the process.

"Live Stretch" includes stretching elastic and bonding the stretched elastic to a substrate. After bonding, the stretched elastic is released causing it to contract, resulting in a "corrugated" substrate. The corrugated substrate can stretch as the corrugated portion is pulled to about the point that the substrate reaches at least one original flat dimension. However, if the substrate is also elastic, then the substrate can stretch beyond the relaxed length of the substrate prior to bonding with the elastic. The elastic is stretched at least 25% of its relaxed length when it is bonded to the substrate.

As used herein, the term "unconstrained caliper" refers to the caliper of the substrate measured according to Edana WSP 120.1 (05), with a circular presser foot having a diameter of 25.40±0.02 mm and an applied force of 2.1 N (i.e. a pressure of 4.14±0.21 kPa is applied).

As used herein, the term "compliant" refers to any material with a durometer hardness of 90 or less as measured according to ASTM International Designation: D2240-05 (Reapproved 2010) for Type M durometers.

As used herein, the term "non-compliant" refers to any material with a hardness value greater than 100 HRBW as defined on the Rockwell B Scale in the American National Standard Designation.

Aspects of the present disclosure involve methods and apparatuses for making elastic laminates, and more particularly, methods and apparatuses for applying fluids onto elastic material positioned on an advancing substrate. The elastic material may be in various forms, such as for example, elastic strands, ribbons, and/or panels. Particular embodiments of the apparatuses and methods disclosed herein provide for the application of viscous fluids, such as adhesives, in pre-determined patterns to elastic material positioned on an advancing substrate. Embodiments of a fluid application apparatus are discussed in more detail below in the context of applying adhesives to an advancing substrate and elastics material. As discussed below, the substrate may have an unconstrained caliper, $H_s$, and has a first surface disposed opposite of a second surface, and the elastic material may have a maximum thickness, $E_t$. The fluid application apparatus may include a slot die applicator and a substrate carrier. The slot die applicator may include a slot opening, a first lip, and a second lip, the slot opening located between the first lip and the second lip. And the substrate carrier may be adapted to advance the substrate and the elastic material past the slot die applicator as the slot die applicator discharges adhesive onto the substrate and the elastic material. In operation, when the first surface of the substrate is disposed on the substrate carrier and the elastic material is positioned on the second surface of the substrate, the substrate carrier advances the second surface of the substrate and the elastic material past the slot opening of the slot die applicator. It is to be appreciated that the apparatus and processes disclosed herein may be used to apply various types of fluids, such as adhesives, in various different patterns to an advancing substrate and elastic materials other than those described and depicted herein.

As discussed in more detail below, the substrate carrier may include a base surface and a pattern element. The pattern element includes a pattern surface and protrudes outward from the base surface. As such, in substrate carriers configured with a base surface, the pattern surface and the base surface are separated by a distance, Hp. In addition, the substrate carrier is positioned adjacent the slot die applicator to define a minimum distance, Hg, between the pattern surface of the pattern element and the first lip and the second lip that is less than the unconstrained caliper, Hs, of the substrate, and wherein a sum of the distance, Hp, and distance, Hg, is greater than the sum of the unconstrained caliper, Hs, of the substrate and the maximum thickness, Et, of the elastic material. Thus, as the substrate carrier advances the second surface of the substrate and elastic material past the slot opening, the pattern element is advanced such that the pattern surface repeatedly advances past the first lip, the slot opening, and the second lip of the slot die applicator. As discussed below, the pattern element and/or the base surface of the substrate carrier may be compliant or compressible. And as such, the pattern element and/or the base surface of the substrate carrier is intermittently compressed as the substrate and elastic material advance between the slot die applicator and the pattern surface. As such, the pattern surface of the pattern element deflects away from the slot die applicator as the substrate, the elastic material, and the pattern element advance past the first lip, the slot opening, and the second lip of the slot die applicator. As the pattern surface is intermittently deflected away from the slot die applicator, adhesive discharged from the slot die applicator is applied onto the elastic material and the second surface of the advancing substrate. More particularly, the adhesive is applied to the elastic material and the substrate in an area having a shape that is substantially the same as a shape defined by the pattern surface.

The apparatuses and methods disclosed herein may include substrate carriers having various configurations. For example, in some embodiments the substrate carrier may be configured as a roller. In other embodiments, the substrate carrier may include an endless belt. The substrate carriers may also utilize various outer surface arrangements. For example, the base surface may be configured as a continuous surface and the substrate carrier may include a plurality of discrete pattern elements separated from each other by the continuous surface. In such a configuration, each pattern element may include a pattern surface and each pattern element may protrude outward from the continuous surface such that each pattern surface is separated from the continuous surface by the distance, Hp. In another example, the pattern surface may be configured as a continuous surface and the base surface may include a plurality of discrete base surfaces separated from each other by the pattern element. In such a configuration, the pattern element may protrude outward from each of the base surfaces such that each base surface is separated from the continuous surface by the distance, Hp. It is to be appreciated that the pattern surface of the pattern element may be configured in various different shapes and sizes and may be configured to define various different patterns. As such, adhesive may be transferred from the slot die applicator to define various patterns on a substrate.

The processes and apparatuses discussed herein may be used to assemble elastic laminates in various types of substrate configurations, some of which may be used in the manufacturing of different types of absorbent articles. To help provide additional context to the subsequent discussion of the process embodiments, the following provides a general description of absorbent articles in the form of diapers that may include elastic laminates that may be assembled in accordance with the methods and apparatuses disclosed herein. Although the methods and apparatuses herein are discussed below in the context of manufacturing absorbent articles, it is to be appreciated that the assembly methods and apparatuses herein may be configured to manufacture various types of elastic laminates.

FIGS. 1 and 2A show an example of a diaper 100 that may include elastic laminates assembled in accordance with the apparatuses and methods disclosed herein. In particular, FIG. 1 shows a perspective view of a diaper pant 100 in a pre-fastened configuration, and FIG. 2A shows a plan view of the diaper pant 100 with the portion of the diaper that faces away from a wearer oriented towards the viewer. The diaper pant 100 shown in FIGS. 1 and 2A includes a chassis 102 and a ring-like elastic belt 104. As discussed below in more detail, a first elastic belt 106 and a second elastic belt 108 are connected together to form the ring-like elastic belt 104.

With continued reference to FIG. 2A, the chassis 102 includes a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 120 in the front waist region 116 and a longitudinally opposing and laterally extending back waist edge 122 in the back waist region 118. To provide a frame of reference for the present discussion, the diaper 100 and chassis 102 of FIG. 2A is shown with a longitudinal axis 124 and a lateral axis 126. In some embodiments, the longitudinal axis 124 may extend through the front waist edge 120 and through the back waist edge 122. And the lateral axis 126 may extend through a first longitudinal or right side edge 128 and through a midpoint of a second longitudinal or left side edge 130 of the chassis 102.

As shown in FIGS. 1 and 2A, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 120 in the front waist region 116 and the laterally extending back waist edge 122 in the back waist region 118. When the diaper pant 100 is worn on the lower torso of a wearer, the front waist edge 120 and the back waist edge 122 of the chassis 102 may encircle a portion of the waist of the wearer. At the same time, the chassis side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562, 646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795, 454; 4,704,115; 4,909,803; U.S. Patent Publication No. 2009/ 0312730A1; and U.S. patent application Ser. No. 13/435,503, entitled "METHODS AND APPARATUSES FOR MAKING LEG CUFFS FOR ABSORBENT ARTICLES", filed on Mar. 30, 2012.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1.

As previously mentioned, the ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2A, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 120 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172.

As shown in FIG. 2A, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2A, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2A.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one exemplary configuration, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

As previously mentioned, the apparatuses and methods according to the present disclosure may be utilized to assemble elastic laminates 402 used in various components of absorbent articles, such as for example, elastic belts 106, 108 and/or leg cuffs 156. Although the following methods may be provided in the context of the diaper 100 shown in FIGS. 1 and 2A, it is to be appreciated that the methods and apparatuses herein may be used to assemble various elastic laminates that can be used with various embodiments of absorbent articles, such as for example, the absorbent articles disclosed in U.S. Pat. No. 7,569,039, filed on Nov. 10, 2004; U.S. Patent Publication No. 2005/0107764A1, filed on Nov. 10, 2004; U.S. patent application Ser. No. 13/221,127, filed on Aug. 30, 2011; and U.S. patent application Ser. No. 13/221,104, filed on Aug. 30, 2011, which are all hereby incorporated by reference herein. In other examples, the fluid application apparatuses and methods herein may be configured to apply adhesives to elastics and substrates to assembly elastic laminates in accordance with the methods and apparatuses disclosed in U.S. patent application Ser. No. 13/434,984, entitled "APPARATUSES AND METHODS FOR MAKING ABSORBENT ARTICLES", filed on Mar. 30, 2012; U.S. patent application Ser. No. 13/435,036, entitled "APPARATUSES AND METHODS FOR MAKING ABSORBENT ARTICLES", filed on Mar. 30, 2012; U.S. patent application Ser. No. 13/435,063, entitled "APPARATUSES AND METHODS FOR MAKING ABSORBENT ARTICLES", filed on Mar. 30, 2012; U.S. patent application Ser. No. 13/435,247, entitled "APPARATUSES AND METHODS FOR MAKING ABSORBENT ARTICLES", filed on Mar. 30, 2012; and U.S. patent application Ser. No. 13/435,503, entitled "METHODS AND APPARATUSES FOR MAKING LEG CUFFS FOR ABSORBENT ARTICLES", filed on Mar. 30, 2012, all of which are incorporated by reference herein.

FIG. 4 shows a perspective view an embodiment of an apparatus 500 for applying adhesives to a substrate and elastic material. It is to be appreciated that the elastic material may be in various forms, such as for example, elastic strands, ribbons, and/or panels. The apparatus 500 includes a slot die applicator 502 and a substrate carrier 504. As shown in FIG. 4, a substrate 506 and elastic material 507 are advancing in a machine direction and are partially wrapped around the substrate carrier 504. More particularly, the substrate 506 includes a first surface 508 disposed opposite a second surface 510. And the first surface 508 of the substrate 506 is disposed on an outer surface 512 of the substrate carrier 504 while the second surface 510 of the substrate 506 advances past the slot die applicator 502. In addition, elastic material 507 is positioned on the second surface 510 of the substrate 506. It is to be appreciated that the elastic material 507 may be in a stretched state when positioned on the substrate 506. As discussed in more detail below, the second surface 510 of the substrate 506 and the elastic material 507 advance past the slot die applicator 502 and adhesive is transferred from the slot die applicator 502 onto the second surface of the substrate and the elastic material in a pattern that is substantially the same as a pattern defined on the outer surface 512 of the substrate carrier 504. As discussed in more detail below, the substrate carrier 504 may be configured in various ways to deposit fluid 530 discharged from a slot die applicator 502 onto a substrate 506 and elastic material 507 in various different patterns, such as shown for example in FIGS. 4A through 4D. As shown in FIGS. 4A and 4B, the elastic material 507 may be positioned on the substrate 506 along a straight path. And as shown in FIGS. 4C and 4D, the elastic material 507 may be positioned on the substrate 506 along a curved path. In addition, the elastic material 507 may be positioned in a stretch state when positioned on the substrate 506.

It is to be appreciated that the slot die applicator 502 shown in FIG. 4 is a generic representation of a device that is used to apply adhesive to the substrate 506. The slot die applicator may include a slot opening 514, a first lip 516, and a second lip 518. The first lip 516 may also be referred to herein as an upstream die lip, and the second lip 518 may also be referred to herein as a downstream die lip. The slot opening 514 is located between the first lip 516 and the second lip 518. Adhesive or other fluid may be discharged from the slot opening 514 onto the second surface 510 of the substrate 506 as the substrate carrier 504 advances the substrate past the first lip 516, slot opening 514, and second lip 518 of the slot die applicator 502. As discussed in more detail below, the substrate 506 and elastic material 507 are also intermittently compressed between the slot die applicator 502 and substrate carrier 504 as the substrate 506 advances past the slot die applicator 502. It is to be appreciated that various forms of slot die applicators may be used herein to apply adhesive or other fluids to an advancing substrate according to methods and apparatuses. For example, U.S. Pat. No. 7,056,386 provides a description of slot die applicators that may be used. Other examples of commercially available slot die applicators include Nordson Corporation's EP11 Series of Slot Die Applicators and ITW Dynatec Gmbh's APEX Series of Slot Die Auto Adhesive Applicators.

Figure 5B:
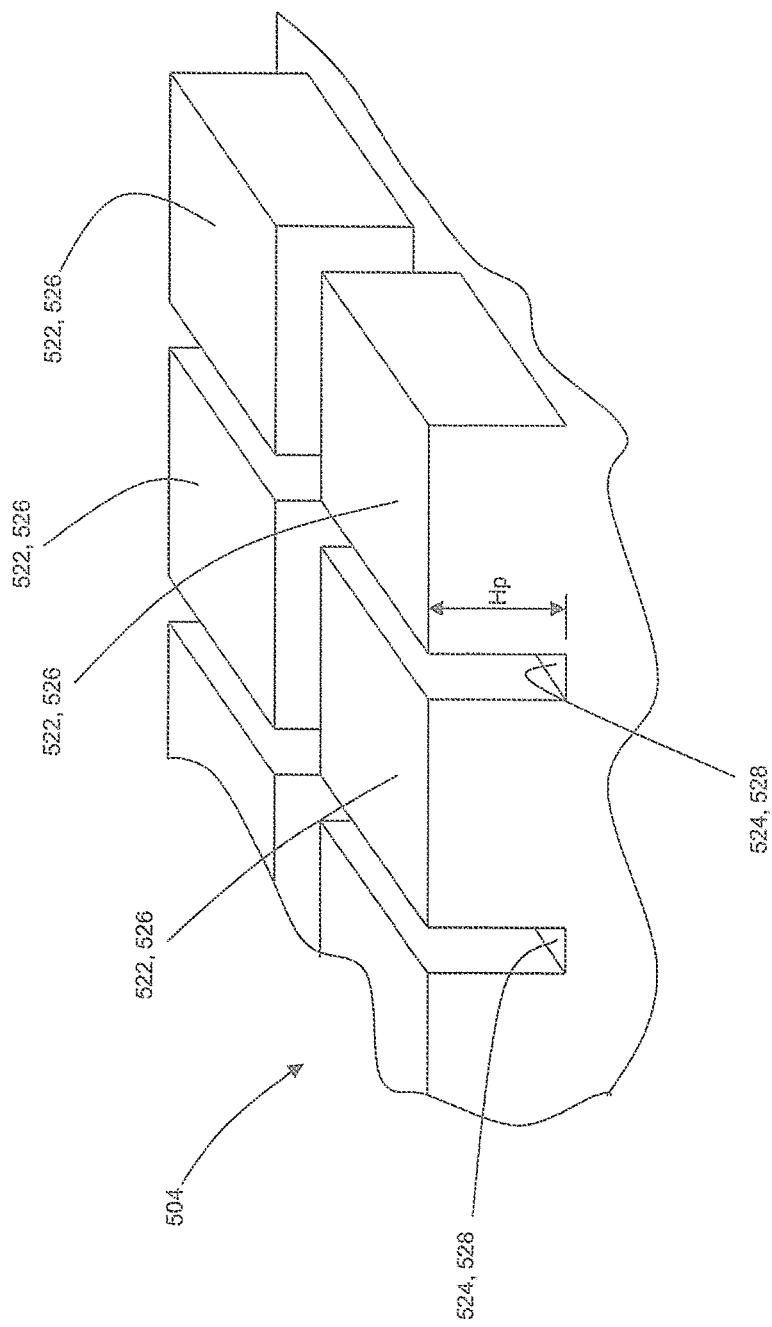
FIG. 5B is a detailed cross-sectional view of the substrate carrier shown in FIG. 5A taken along the line 5B-5B.

Various types of substrate carriers 504 may be used in accordance with the apparatuses and methods herein. For example, FIGS. 5A and 5B show an embodiment of a substrate carrier 504 configured as a roller 520 adapted to advance a substrate 506 past the slot die applicator 502. The outer surface 512 of the substrate carrier 504 shown in FIGS. 5A and 5B includes a plurality of pattern elements 522 that protrude radially outward from a base surface 524. Each pattern element 522 includes a pattern surface 526, and the radial protrusion of the pattern elements 522 from the base surface 524 define a distance, Hp, between the pattern surface 526 and the base surface 524. As shown in FIGS. 5A and 5B, the base surface 524 is configured as a continuous surface 528, and the plurality of discrete pattern elements 522 are separated from each other by the continuous surface 528. The pattern surfaces 526 in FIGS. 5A and 5B define a diamond shape. In some embodiments, the shape and size of the pattern surface 526 of each pattern element 522 may be identical or substantially identical to each other. It is to be appreciated that the number, size, and shape of some or all the pattern surfaces and/or pattern elements may be different. In addition, the distance, Hp, between the base surface 524 and the pattern surface 526 of the pattern element 522 may be the same or different for some or all of the pattern elements.

As discussed in more detail below, as the substrate carrier 504 advances the substrate 506 past the slot die applicator 502, fluid discharged from the slot die applicator is deposited onto the substrate in a pattern substantially matching the shapes of the pattern surfaces on the substrate carrier. For example, FIG. 5C shows an example pattern of fluid 530 deposited on a second surface 510 of a substrate 506 and elastic material 507 after being advanced past a slot die applicator while disposed on a substrate carrier having pattern elements 522 and pattern surfaces 526 similar to those shown in FIGS. 5A and 5B. As shown in FIG. 5C, the fluid 530 is deposited onto the substrate 506 and the elastic material in discrete pattern areas 532 having diamond shapes that correspond with and may mirror the shapes of the pattern surfaces 526 on the substrate carrier 504 shown in FIG. 5A.

Figure 6B:
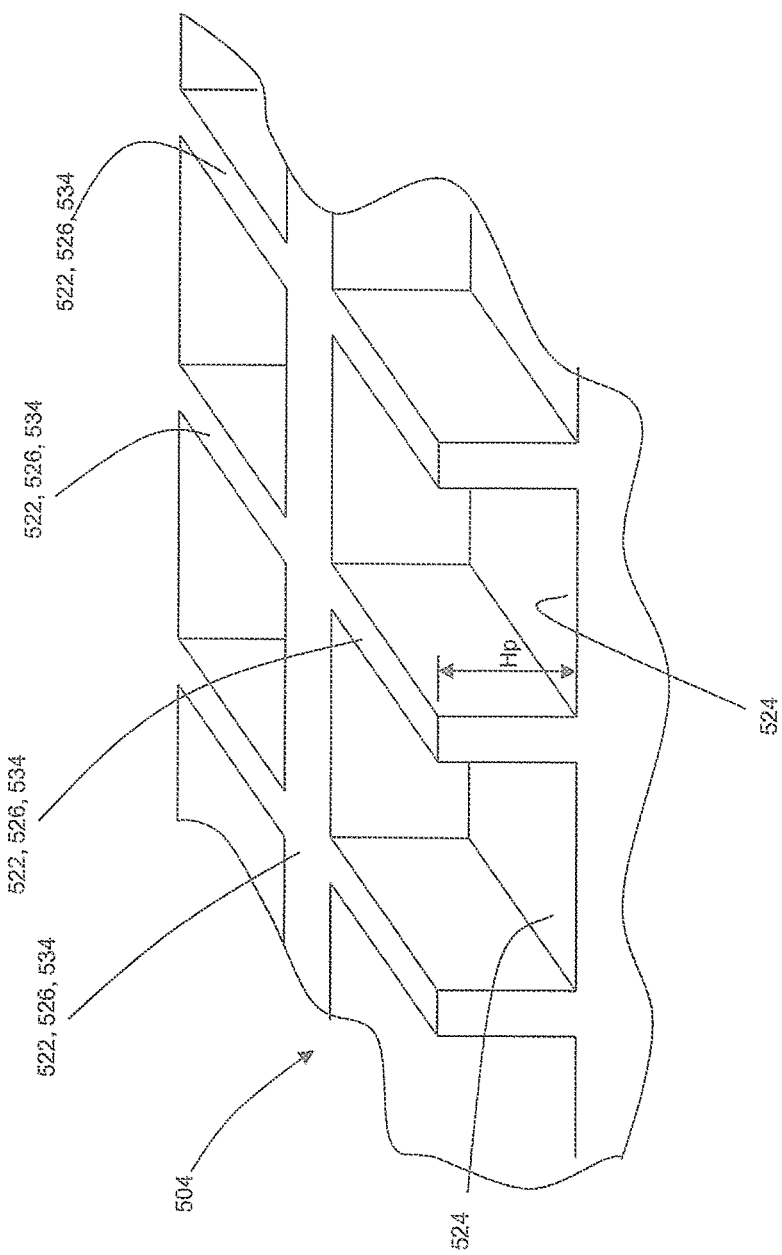
FIG. 6B is a detailed cross-sectional view of the substrate carrier shown in FIG. 6A taken along the line 6B-6B.

FIGS. 6A and 6B show another embodiment of a substrate carrier 504 configured as a roller 520 adapted to advance a substrate 506 past the slot die applicator 502. The substrate carrier 504 shown in FIGS. 6A and 6B includes a single pattern element 522 including a pattern surface 526. And the pattern element 522 protrudes radially outward from a plurality of base surfaces 524. More particularly, the pattern surface 526 is configured as a continuous surface 534 and the plurality of base surfaces are separated from each other by the pattern element 522. The radial protrusion of the pattern element 522 from the base surfaces 524 defines a distance, Hp, between the pattern surface 526 and the base surfaces 524. The pattern surface 526 in FIGS. 6A and 6B defines a continuous crossing line pattern wherein the shape and size of each base surface 524 are identical or substantially identical to each other. It is to be appreciated that the number, size, and shape of some or all the base surfaces may be different. In addition, the distance, Hp, between the base surfaces 524 and the pattern surface 526 of the pattern element 522 may be the same or different for some or all of the base surfaces. It should also be appreciated that the substrate carrier may be configured without base surfaces. For example, the substrate carrier may include a plurality of holes and the pattern surface may be configured as a continuous surface wherein the plurality of holes are separated from each other by the pattern element.

As previously mentioned, as the substrate carrier 504 advances the substrate 506 past the slot die applicator 502, fluid 530 discharged from the slot die applicator 502 is deposited onto the substrate 506 in a pattern substantially matching the shape of the pattern surface 526 on the substrate carrier 504. For example, FIG. 6C shows an example pattern of fluid 530 deposited on a second surface 510 of a substrate 506 and elastic material 507 after being advanced past a slot die applicator 502 while disposed on a substrate carrier 504 having a pattern element 522 and pattern surface 526 similar to that shown in FIGS. 6A and 6B. As shown in FIG. 6C, the fluid 530 is deposited onto the substrate 506 and the elastic material 507 in a crossing line pattern defining diamond shapes therebetween that correspond with and may mirror the shapes of the base surfaces 524 on the substrate carrier 504 shown in FIGS. 6A and 6B.

As previously mentioned, the substrate carrier may be constructed in various ways such that the base surface and/or pattern elements may include compliant materials. In some configurations, the compliant material(s) may be compressible to allow a pattern surface of a pattern element to deflect away from the slot die applicator. Thus, the substrate carrier may be configured such that deflection of the pattern surface away from the slot die applicator compresses the pattern element and/or base surface as the substrate, elastic material, and pattern element advance past the first lip, the slot opening, and the second lip of the slot die applicator.

Figure 7:
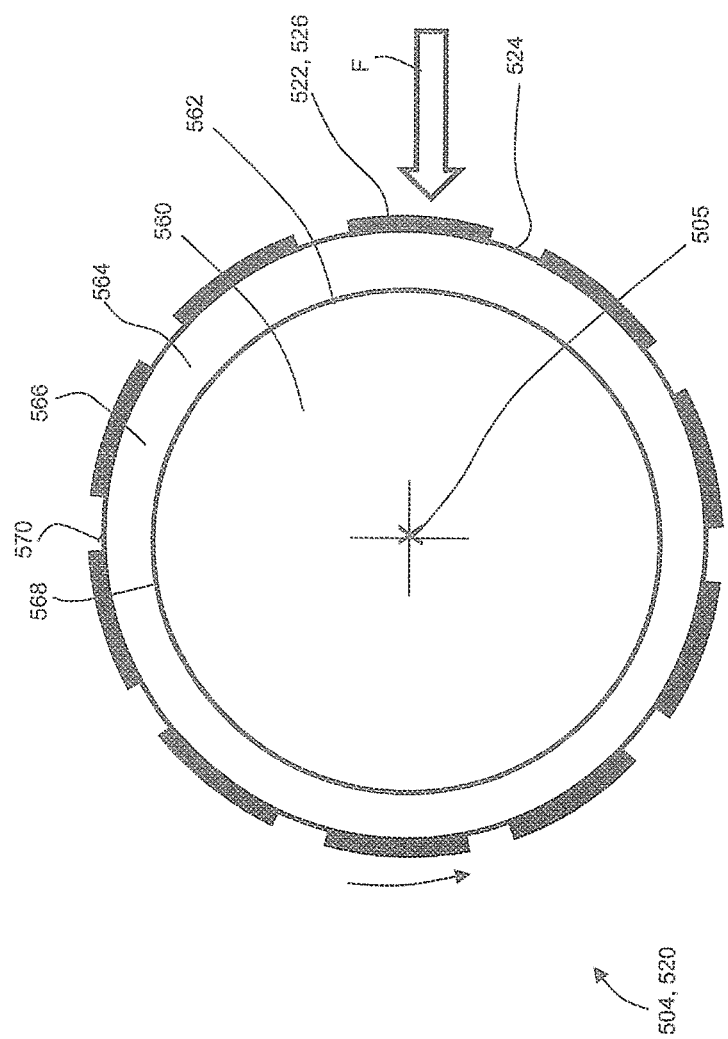
FIG. 7 is a schematic cross-sectional side view of an example substrate carrier.

FIG. 7 shows a schematic cross-sectional side view of an example substrate carrier 504 that may be configured with compliant materials and components that can be compressed and allow the pattern surface 526 to deflect in response to a force or forces, F, exerted on the pattern surface 526. The substrate carrier 504 in FIG. 7 is in the form of a roller 520 adapted to rotate around an axis of rotation 505. In operation, a force or forces, F, may be exerted on the pattern surface 526 as the substrate 506, elastic material 507, and pattern element 522 advance past the first lip 516, the slot opening 514, and the second lip 518 of the slot die applicator 502. It is to be appreciated that the substrate carrier 504 may be configured in various ways with various different components of compliant materials that allow the pattern surface 526 to deflect.

For example, FIGS. 7A1 and 7A2 show a detailed view of the substrate carrier 504 in the form of a roller 520, such as from FIG. 7, including a compliant pattern element 522 and a compliant base surface 524 connected with a base roll 560 having a non-compliant support surface 562. More particularly, the roller 520 in FIGS. 7A1 and 7A2 may include a base layer 564 of compliant material extending radially outward from the non-compliant support surface 562 to define the compliant base surface 524. In some arrangements, the base layer 564 of compliant material may be formed as a cylindrically shaped sleeve or tube 566 having an inner radial surface 568 and an outer radial surface 570. The inner radial surface 568 may surround all or a portion of the non-compliant support surface 562 of the base roll 560, and the outer radial surface 570 may define all or a portion of the base surface 524. In turn, the pattern element 522 may include a proximal end portion 572 and a distal end portion 574 that includes the pattern surface 526, wherein the proximal end portion 572 is connected with outer radial surface 570 of the base layer 564. As such, the pattern element 522 may extend radially outward from the base layer 564 of compliant material to the distal end portion 574. It is to be appreciated that the pattern element 522 may be separately connected with or integrally formed with the compliant base layer 564. FIG. 7A1 shows the pattern element 522 and base layer 564 of compliant material in an uncompressed state, wherein the minimum distance between the pattern surface 526 and the non-compliant support surface 562 is defined by distance, R1. FIG. 7A2 shows the compliant pattern element 522 and compliant base layer 564 of FIG. 7A1 in a compressed state wherein a force or forces, F, are applied to the pattern surface 526. Because the pattern element 522 and base layer 564 are both compliant, the force or forces, F, applied to the pattern surface 526 causes the pattern element 522 and the base layer 564 to be compressed against the non-compliant surface 562 of the base roll 560. The compression of the pattern element 522 and the base layer 564 allows the pattern surface 526 to deflect in response to the forces, F. As such, the minimum distance between the pattern surface 526 and the non-compliant surface 562 is defined as distance, R2, wherein R2 is less than R1.

In another example, FIGS. 7B1 and 7B2 show a detailed view of the substrate carrier 504 in the form of a roller 520, such as from FIG. 7, including a non-compliant pattern element 522 and a compliant base surface 524 connected with a base roll 560 having a non-compliant support surface 562. More particularly, the roller 520 in FIGS. 7B1 and 7B2 may include a base layer 564 of compliant material extending radially outward from the non-compliant support surface 562 to define the compliant base surface 524. In some arrangements, the base layer 564 of compliant material may be formed as a cylindrically shaped sleeve or tube 566 having an inner radial surface 568 and an outer radial surface 570. The inner radial surface 568 may surround all or a portion of the non-compliant support surface 562 of the base roll 560, and the outer radial surface 570 may define all or a portion of the base surface 524. In turn, the pattern element 522 may include a proximal end portion 572 and a distal end portion 574 that includes the pattern surface 526, wherein the proximal end portion 572 is connected with outer radial surface 570 of the base layer 564. As such, the pattern element 522 may extend radially outward from the base layer 564 of compliant material to the distal end portion 574. It is to be appreciated that the pattern element 522 may be separately connected with or integrally formed with the compliant base layer 564. FIG. 7B1 shows the base layer 564 of compliant material in an uncompressed state, wherein the minimum distance between the pattern surface 526 and the non-compliant support surface 562 is defined by distance, R1. FIG. 7B2 shows the compliant base layer 564 of FIG. 7B1 in a compressed state wherein a force or forces, F, are applied to the pattern surface 526. Because the pattern element 522 is non-compliant and the base layer 564 is compliant, the force or forces, F, applied to the pattern surface 526 causes the pattern element 522 to push against the base layer 564 such that the base layer 564 is compressed between the pattern element 522 and the non-compliant surface 562 of the base roll 560. The compression of the base layer 564 allows the pattern surface 526 to deflect in response to the force or forces, F. As such, the minimum distance between the pattern surface 526 and the non-compliant surface 562 is defined as distance, R2, wherein R2 is less than R1.

In yet another example, FIGS. 7C1 and 7C2 show a detailed view of the substrate carrier 504 in the form of a roller 520 from FIG. 4 including a compliant pattern element 522 connected with a base roll 560. The base roll 560 includes a non-compliant outer circumferential support surface 562 that also defines the base surface 524. In turn, the pattern element 522 may include a proximal end portion 572 and a distal end portion 574 that includes the pattern surface 526, wherein the proximal end portion 572 is connected with non-compliant support surface 562. FIG. 7C1 shows the pattern element 522 in an uncompressed state, wherein the minimum distance between the pattern surface 526 and the non-compliant support surface 562 is defined by distance, R1. FIG. 7C2 shows the pattern element 522 of FIG. 7C1 in a compressed state wherein a force or forces, F, are applied to the pattern surface 526. Because the pattern element 522 is compliant, the force or forces, F, applied to the pattern surface 526 causes the pattern element 522 to be compressed against the non-compliant support surface 562 of the base roll 560. The compression of the pattern element 522 allows the pattern surface 526 to deflect in response to the force or forces, F. As such, the minimum distance between the pattern surface 526 and the non-compliant support surface 562 is defined as distance, R2, wherein R2 is less than R1. In some instances, the force or forces, F, may be exerted in a radial direction toward the axis of rotation 505.

Figure 8:
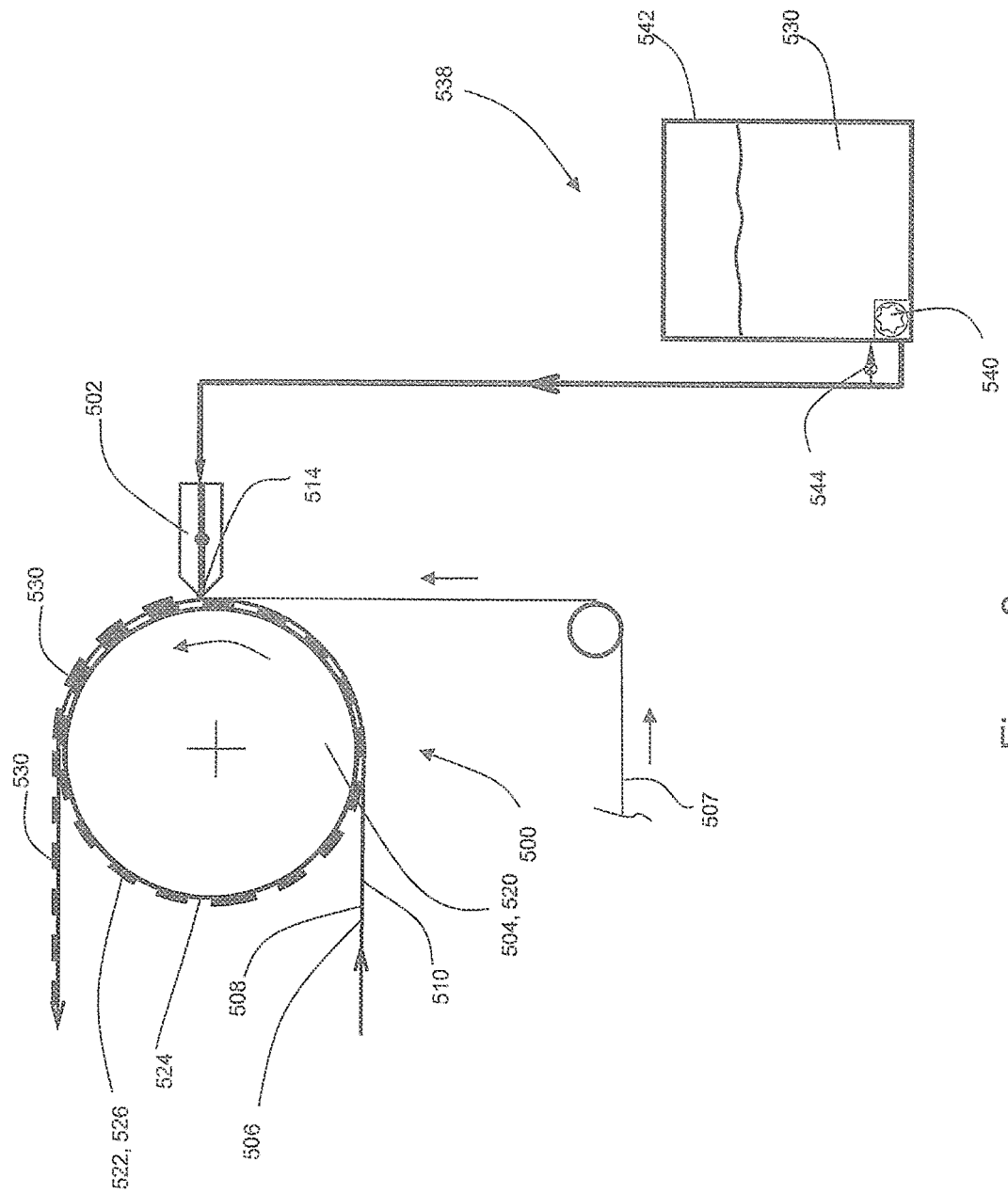
FIG. 8 is a schematic cross-sectional side view of a fluid application apparatus applying fluid to a substrate and elastic material.

As previously mentioned, the methods and apparatuses herein include a substrate carrier adapted to advance a substrate and elastic material past a slot die applicator. FIG. 8 shows a schematic cross-sectional side view of an embodiment of a fluid application apparatus 500 including a substrate carrier 504 and a slot die applicator 502. The substrate 506 includes a first surface 508 and a second surface 510 disposed opposite the first surface 508. A portion of the first surface 508 of the substrate 506 is disposed on the substrate carrier 504, which may be configured as a roller 520 having a plurality of pattern elements 522 protruding from a plurality of base surfaces 524. Advancing elastic material 507 is also positioned on the second surface 510 of the substrate 506. It is to be appreciated that the substrate carrier 504 shown in FIG. 8 may be configured with various features and aspects of any substrate carriers discussed herein, including those discussed above with reference to FIGS. 4 through 7C2. The roller 520 rotates to advance the second surface 510 of the substrate 506 and elastic material 507 past the slot die applicator 502. It is also to be appreciated that the substrate carrier 504 may be configured to advance the substrate 506 at a faster speed than the elastic material 507 upstream of the substrate carrier 504. As such, the elastic material 507 may be stretched while being positioned on the substrate 506. For example, with reference to FIG. 8, the roller 520 may be configured to advance the second surface 510 of the substrate 506 past the slot die applicator 502 at a speed of V1. And the elastic material 507 upstream of the slot die applicator 502 is advancing at a speed V2, wherein V1 is greater than V2. Thus, the elastic material 507 may be stretched while being positioned on the second surface 510 of the substrate 506.

A fluid delivery system 538 may be used to supply fluid 530, such as an adhesive, to the slot die applicator 502. It is to be appreciated that the fluid delivery system may be configured in various different ways. For example, as shown in FIG. 8, the fluid delivery system 538 may include a pump 540 to move fluid from a tank 542 to the slot die applicator 502. The fluid delivery system 538 may also be configured with a pressure relief valve 544 configured to help control the pressure of the fluid 530 fed from the pump 540. Fluid 530 from the fluid delivery system 538 passes through the slot die applicator 502 and slot opening 514 and is transferred to the second surface 510 of the advancing substrate 506 and elastic material 507.

With continued reference to FIG. 8, fluid 530 passing from the slot die applicator 502 is transferred to the second surface 510 of the substrate 506 and the elastic material 507 in a pattern or shape that is substantially the same as the pattern surfaces 526 on the substrate carrier 504. As discussed in more detail below, the substrate carrier 504 is positioned adjacent the slot die applicator 502 to define a minimum distance between the pattern surface 526 and slot die applicator 502, which is less than the sum of the maximum thickness of the elastic material 507 and the unconstrained caliper of the substrate 506. In some configurations, the minimum distance between the pattern surface 526 and slot die applicator 502 may be less than the unconstrained caliper of the substrate 506. As such, the pattern element and/or base surface may be compressed to allow the pattern surface 526 of the pattern element to deflect away from the slot die applicator 502 as the substrate 506, elastic material 507, and pattern surface 526 of the pattern element 522 advance past the first lip 516, the slot opening 514, and the second lip 518 of the slot die applicator 502. However, the minimum distance between the base surface 524 of the substrate carrier 504 and the slot die applicator 502 is greater than the sum of the maximum thickness of the elastic material 507 and the unconstrained caliper of the substrate 506. As such, the base surface 524 is not compressed as the substrate and elastic material advances past the first lip 516, the slot opening 514, and the second lip 518 of the slot die applicator 502. Thus, in operation, although fluid 530 is continuously discharged from the slot die applicator 502, fluid 530 is transferred to the advancing substrate 506 and elastic material 507 when the pattern element 522 and/or base surface 524 is compressed as pattern surfaces 526 on the substrate carrier 502 advance past the slot die opening 514 and deflect the pattern surface 526. And fluid 530 is not transferred to the advancing substrate 506 and elastic material 507 when the pattern element 522 and/or base surface 524 are uncompressed while the base surfaces 524 on the substrate carrier 504 advance past the slot die opening 514.

Figure 8C:
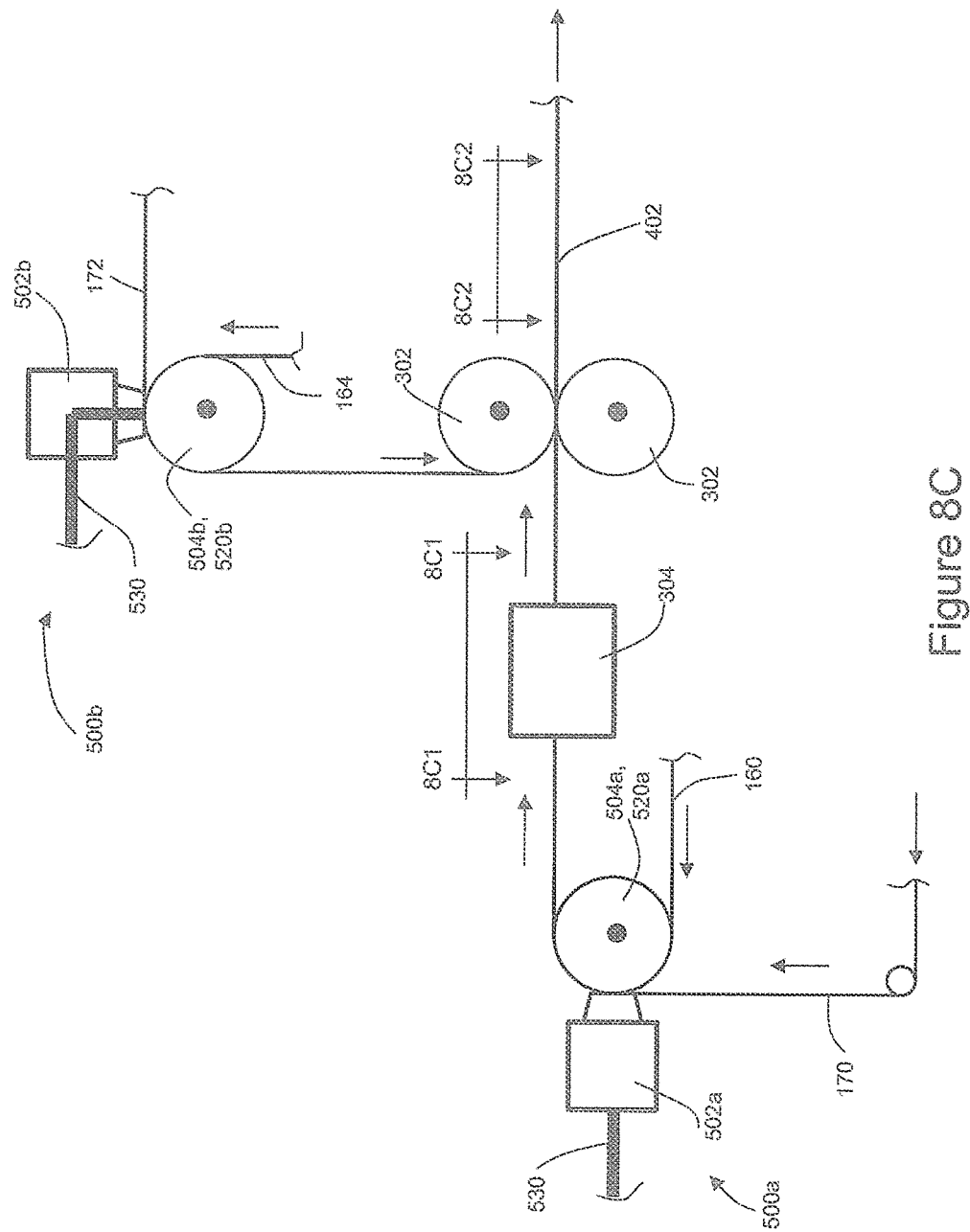
FIG. 8C is a schematic side view of a third converting configuration for making an elastic laminate.

As mentioned above, the method and apparatuses may be used to apply elastic material to substrates to make elastic laminates. It is to be appreciated that the elastic laminates may be made in various ways and may be further modified for incorporation into various types of articles. For example, FIGS. 8A through 8C2 show various examples of how the methods and apparatuses herein may be used to make elastic laminates for use in absorbent articles. More particularly, FIGS. 8A through 8C2 are described below in the context of making elastic laminates in the form of belt materials 402 that may be used in the assembly of the elastic belts 106, 108 described above with reference to FIGS. 1 through 3B.

As shown in FIGS. 8A and 8A1, a first continuous substrate layer in the form of a continuous length of outer layer belt material 162; a second continuous substrate layer in the form of a continuous length of inner layer belt material 164; and elastics 168 are combined to form a continuous elastic laminate in the form of a belt material 402. The elastics 168 shown in FIGS. 8A and 8A1 may be in the form of outer elastic strands 170 and inner elastic strands 172. As discussed below, a fluid application apparatus 500, which includes a slot die applicator 502 and substrate carrier 504, may be used to apply adhesive the elastics 168 and outer belt material 162 as discussed above with reference to the substrate 506 and elastic material 107. With continued reference to FIGS. 8A and 8A1, the continuous length of outer layer belt material 162 is advanced in a machine direction onto a substrate carrier 504, which is depicted as a roller 520. Stretched outer elastic strands 170 and inner elastic strands 172 advance in a machine direction and are combined with the outer layer belt material 162 at the substrate carrier 504. The combined outer layer belt material 162 and elastic strands 170, 172 advance on the rotating roller 520 past a slot die applicator 502. In turn, the slot die applicator 502 applies adhesive to the outer layer belt material 162 and elastic strands 170, 172, such as described above with reference to FIGS. 4-8. Referring back to FIGS. 8A and 8A1, the outer belt material 162 and elastics 170, 172 advance from the substrate carrier 504 in a machine direction and are combined with a continuous inner layer belt material 164 at nip rolls 302 to form a continuous length of belt material 402. It is to be appreciated that the fluid application apparatus 500 may be configured to apply adhesive in various ways to the elastic strands 170, 172 as well as either or both of the continuous lengths of outer layer belt material 162 and inner layer belt material 164 before entering nip rolls 502. For example, adhesive 530 may be applied continuously along the lengths of outer layer belt material 162 and outer elastic strands 170, and adhesive may be applied intermittently along the lengths of the inner elastic strands 172 and/or intermittently along the continuous length of outer layer belt material 162.

As shown in FIG. 8A1, the inner elastic strands 172 are intermittently bonded to either or both of the continuous lengths of outer layer belt material 162 and inner layer belt material 164 along the machine direction MD. More particularly, as shown in FIG. 8A1, the belt material 402 may include non-bonded regions 403 intermittently spaced between bonded regions 405 along the machine direction MD. Thus, the inner elastic strands 172 are not bonded to either the outer layer belt material 162 or inner layer belt material 164 in the non-bonded regions 403. And the inner elastic strands 172 are bonded to the outer layer belt material 162 and/or inner layer belt material 164 in the bonded regions 405. For the purposes of clarity, dashed lines 401 are shown in FIG. 8A1 to represent example boundaries between the non-bonded regions 403 and the bonded regions 405. It is to be appreciated that such boundaries between the non-bonded regions 403 and the bonded regions 405 can also be curved, angled, and/or straight. Although the inner elastic strands 172 are not bonded to the either the outer layer belt material 162 or inner layer belt material 164 in the non-bonded regions 403, adhesive 530 may be applied in areas between the individual inner elastic strands 172 to bond the outer layer belt material 162 and inner layer belt material 164 together in the non-bonded regions 403.

Although FIG. 8A shows an embodiment wherein the belt material 402 is formed by combining continuous lengths of outer layer belt material 162 and inner layer belt material 164 with elastic strands 168, it is to be appreciated the belt material 402 can be formed in various other ways. For example, the belt material 402 may be formed by a folding portion of a single continuous substrate onto another portion of the single continuous substrate. For example, FIGS. 8B and 8B1 show a configuration wherein the belt material 402 is formed by combining continuous lengths of elastic strands 168 with a single continuous length of belt material 160 having a first surface 161a and an opposing second surface 161b. More particularly, the continuous lengths of stretched outer elastic strands 170 and inner elastic strands 172 are advanced in a machine direction MD and combined with the first surface 161a of the belt material 160 at a substrate carrier 504. The combined belt material 160 and elastic strands 170, 172 advance on the rotating roller 520 past a slot die applicator 502. In turn, the slot die applicator 502 applies adhesive 530 to the belt material 160 and elastic strands 170, 172, such as described above with reference to FIGS. 4-8. Referring back to FIGS. 8B and 8B1, the belt material 160 and elastics 170, 172 advance from the substrate carrier 504 in a machine direction to a folding apparatus 304 adapted to fold a portion of the first surface 161a of the belt material 160 onto another portion of the first surface 161a such that the elastics 170, 172 are intermittently bonded between the folded portions of the belt material 160. In the arrangement shown in FIGS. 8B and 8B1, adhesive 530 may be applied intermittently to the elastic strands 170, 172 and/or the continuous length of belt material 160 before entering the folder 304. For example, FIG. 8B1 shows an arrangement wherein the belt material 160 includes opposing longitudinal edges 160a, 160b and laterally opposed edge regions 166a, 166b separated by a central region 166c. And the elastics are combined with the central region 166c of the first surface 161a of the belt material 160. The folder 304 folds the opposing edge regions 166a, 166b onto the central region 166c. As such, the elastics are sandwiched between the first surface 161a of the opposing edge regions 166a, 166b and the first surface 161a of the central region 166c. Thus, an elastic laminate 402 can be formed wherein a first substrate layer may comprise the central region 166c, and wherein a second substrate layer may comprise the folded edge regions 166a, 166b.

It is to be appreciated that the belt material may be folded in various ways at the folder 304. For example, in some embodiments, the elastics 168 may be combined with the belt material 160 in such a way that the folder 304 need only fold the belt material 160 once along the center region 166c. For example, the folder 304 may fold the first surface 161a of the belt material 160 onto itself such that the first longitudinal edge 161a is aligned with the second longitudinal edge 161b.

Yet another example configuration is shown in FIGS. 8C through 8C2 that utilizes a first fluid application device 500a and a second fluid application device 500b. In particular, the belt material 402 is formed by first combining continuous lengths of outer elastic strands 170 with the opposing edge regions 166a, 166b of single continuous length of belt material 160 at a first substrate carrier 504a in the form of a roller 520a. Before being combined at roller 520a, the outer elastic strands 170 are stretched in the machine direction MD. The first slot die applicator 502a applies adhesive 530 to the elastics 170 and belt material 160 while advancing on the rotating roller 520a. From the roller 520a, the combined elastics 170 and the belt material 160 advance to a folding apparatus 304 adapted to fold the opposing edge regions 166a, 166b onto themselves. As such, the outer elastics 170 are sandwiched between first surfaces 161a of the opposing edge regions 166a, 166b, such as shown in FIG. 8C1. Referring back to FIG. 8C, stretched inner elastics 172 and the inner belt material 164 are combined at a second substrate carrier 504b in the form of a roller 520b. The second slot die applicator 502b applies adhesive 530 to the elastics 172 and belt material 164 while advancing on the rotating roller 520b. From the roller 520b, the advancing inner elastics 172 and inner belt material 164 are combined with the outer elastics 170 and belt material 160 at nip rolls 302 to form the belt material 402 as shown in FIG. 8C2. Thus, an elastic laminate can be formed wherein the first substrate layer may comprise portion of the folded edge regions 166a, 166b and/or the central region 166c, and wherein the second substrate layer may comprise portions of the folded edge regions 166a, 166b and/or the central region 166c, and the belt material 164.

In some converting configurations, the elastic laminate 402 may be subjected to various additional operations, such as described in U.S. patent application Ser. No. 13/434,984, entitled "APPARATUSES AND METHODS FOR MAKING ABSORBENT ARTICLES", filed on Mar. 30, 2012; U.S. patent application Ser. No. 13/435,036, entitled "APPARATUSES AND METHODS FOR MAKING ABSORBENT ARTICLES", filed on Mar. 30, 2012; U.S. patent application Ser. No. 13/435,063, entitled "APPARATUSES AND METHODS FOR MAKING ABSORBENT ARTICLES", filed on Mar. 30, 2012; U.S. patent application Ser. No. 13/435,247, entitled "APPARATUSES AND METHODS FOR MAKING ABSORBENT ARTICLES", filed on Mar. 30, 2012; and U.S. patent application Ser. No. 13/435,503, entitled "METHODS AND APPARATUSES FOR MAKING LEG CUFFS FOR ABSORBENT ARTICLES", filed on Mar. 30, 2012, all of which are incorporated by reference herein. For example, a cutting unit may intermittently deactivate the elastics 172 in by severing, cutting, and/or breaking the inner elastics 172 in the non-bonded regions 403. As such, severed ends of the inner elastics 172 may retract or snap back to the bonded regions 405.

Figure 9A:
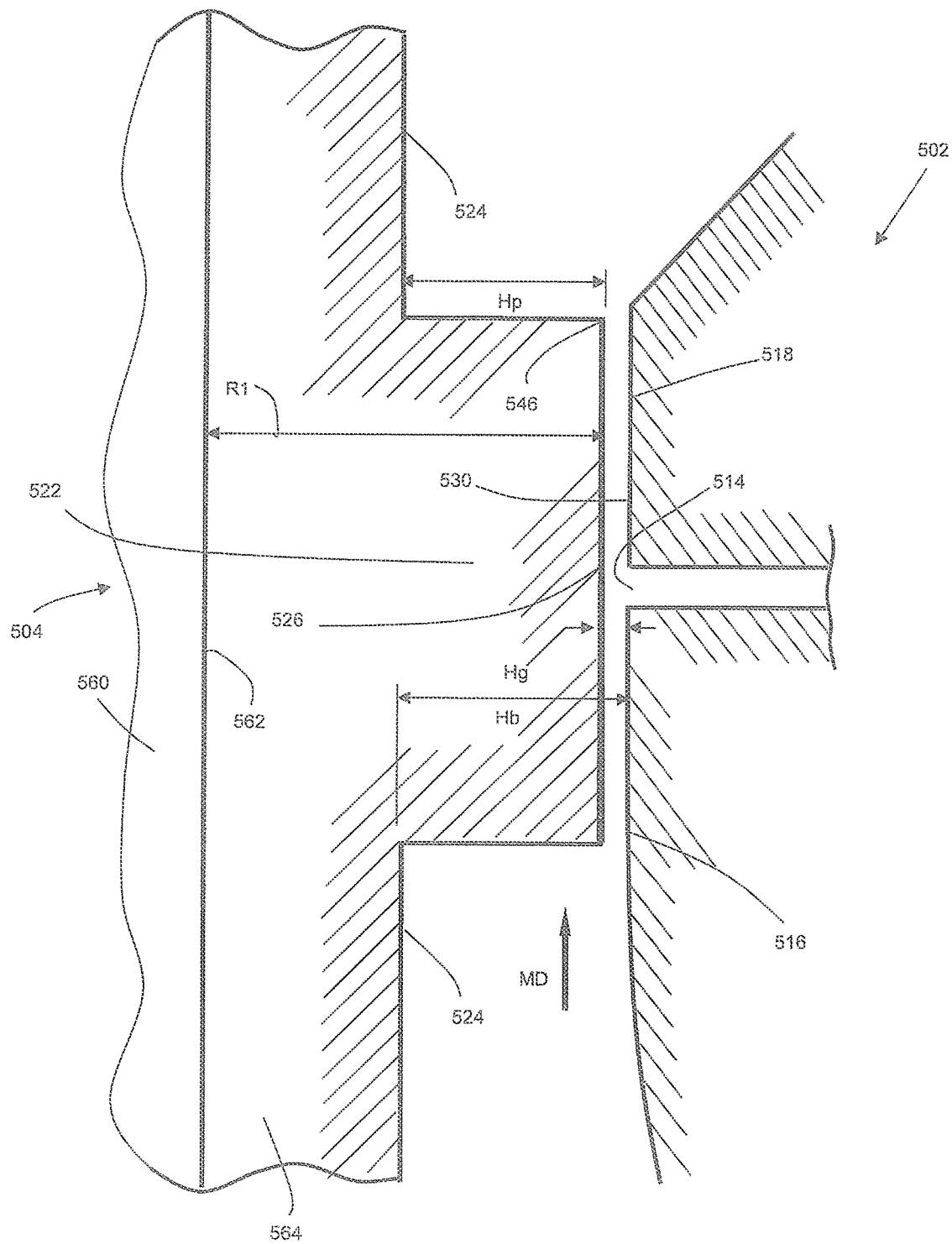
FIG. 9A is a detailed cross-sectional view of the substrate carrier of FIG. 8 without the substrate and elastic material wherein the pattern surface of a pattern element is adjacent a first lip, a second lip, and slot opening of the slot die applicator.

A more detailed description of fluid transfer from the slot die applicator 502 to the substrate 506 and elastic material 507 is provided with reference to FIGS. 9A through 9E. FIG. 9A is a detailed cross-sectional view of the substrate carrier of FIG. 8 shown without the substrate 506 and elastic material 507 wherein the pattern surface 526 of a pattern element 522 is adjacent a first lip 516, a second lip 518, and slot opening 514 of the slot die applicator 502. As shown in FIG. 9A, the substrate carrier 504 includes a non-compliant support surface 562, a base surface 524, and a pattern element 522 protruding from base surface 524. In an uncompressed state, the pattern element 522 protrudes outward from the base surface 524 to define a distance, Hp, between the pattern surface 526 and the base surface 524, and to define a minimum distance, R1, between the pattern surface 526 and the non-compliant support surface 562. The substrate carrier 504 is also positioned adjacent the slot die applicator 502 to define a minimum distance, Hg, between the pattern surface 526 of the uncompressed pattern element 522 and the first lip 516 and the second lip 518. As discussed below, the minimum distance, Hg, is less than the sum of the unconstrained caliper, Hs, of the substrate 506 and the maximum thickness, Et, of the elastic material 507 advanced by the substrate carrier 504. In addition, the substrate carrier 504 is positioned adjacent the slot die applicator 502 to define a minimum distance, Hb, between the base surface 524 and the first lip 516 and the second lip 518. As discussed below, the minimum distance, Hb, may be greater than the sum of the unconstrained caliper, Hs, of the substrate 506 and the maximum thickness, Et, of the elastic material 507 advanced by the substrate carrier 504.

Figure 9B:
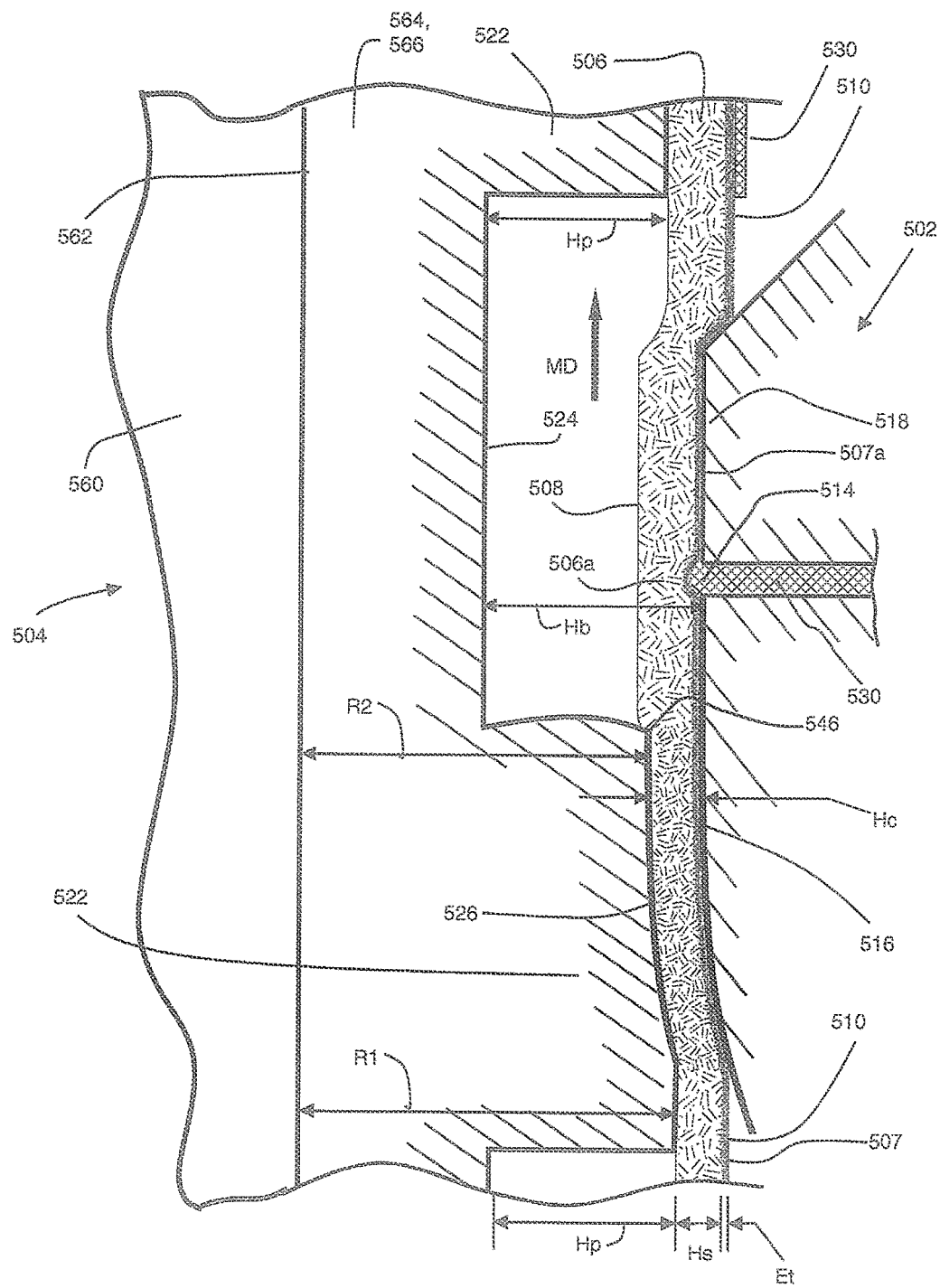
FIG. 9B is a detailed cross-sectional view of a substrate carrier, a substrate, and an elastic material advancing past a slot die applicator and showing the substrate and elastic material between a slot opening of the slot die applicator and an advancing base surface.

FIG. 9B is a detailed cross-sectional view of a substrate carrier 504 of FIG. 9A and a substrate 506 and elastic material 507 advancing past a slot die applicator 502. The substrate 506 has an unconstrained caliper, Hs, and has a first surface 508 disposed opposite of a second surface 510. An elastic material 507 is positioned on the second surface 510 of the substrate 506. The first surface 508 of the substrate 506 is disposed on the substrate carrier 504. And the substrate 506, elastic material 507, and substrate carrier 504 are shown as advancing together in a machine direction, MD, past the slot die applicator 502. More particularly, the second surface 510 of the substrate 506 and the elastic material 507 are advancing past a slot opening 514 located between an upstream lip 516 and a downstream lip 518 of the slot die applicator 502. As previously mentioned, the substrate carrier 504 is positioned adjacent the slot die applicator 502 to define a minimum distance, Hg, between the pattern surface 526 of the uncompressed pattern element 522 and the first lip 516 and the second lip 518 that is less than the sum of the maximum thickness, Et, of the elastic material 507 and the unconstrained caliper, Hs, of the substrate 506. In addition, the substrate carrier 504 is positioned adjacent the slot die applicator 502 to define a minimum distance, Hb, between the base surface 524 and the first lip 516 and the second lip 518 that is greater than the sum of the maximum thickness, Et, of the elastic material 507 and unconstrained caliper, Hs, of the substrate 506. The apparatus 500 may also be configured such that a sum of the distance, Hp, and distance, Hg, is greater than the sum of the unconstrained caliper, Hs, of the substrate 506 and the maximum thickness, Et, of the elastic material 507. Thus, a portion 506a, 507a of the substrate 506 and the elastic material 507 that is located between the slot opening 514 of the slot die applicator 502 and the advancing base surface 524 is not pressed against the base surface 524. As such, although fluid 530 is continuously discharged from the slot opening 514, fluid 530 is not being transferred to the second surface 510 of the substrate 506 and the elastic material 507.

Figure 9C:
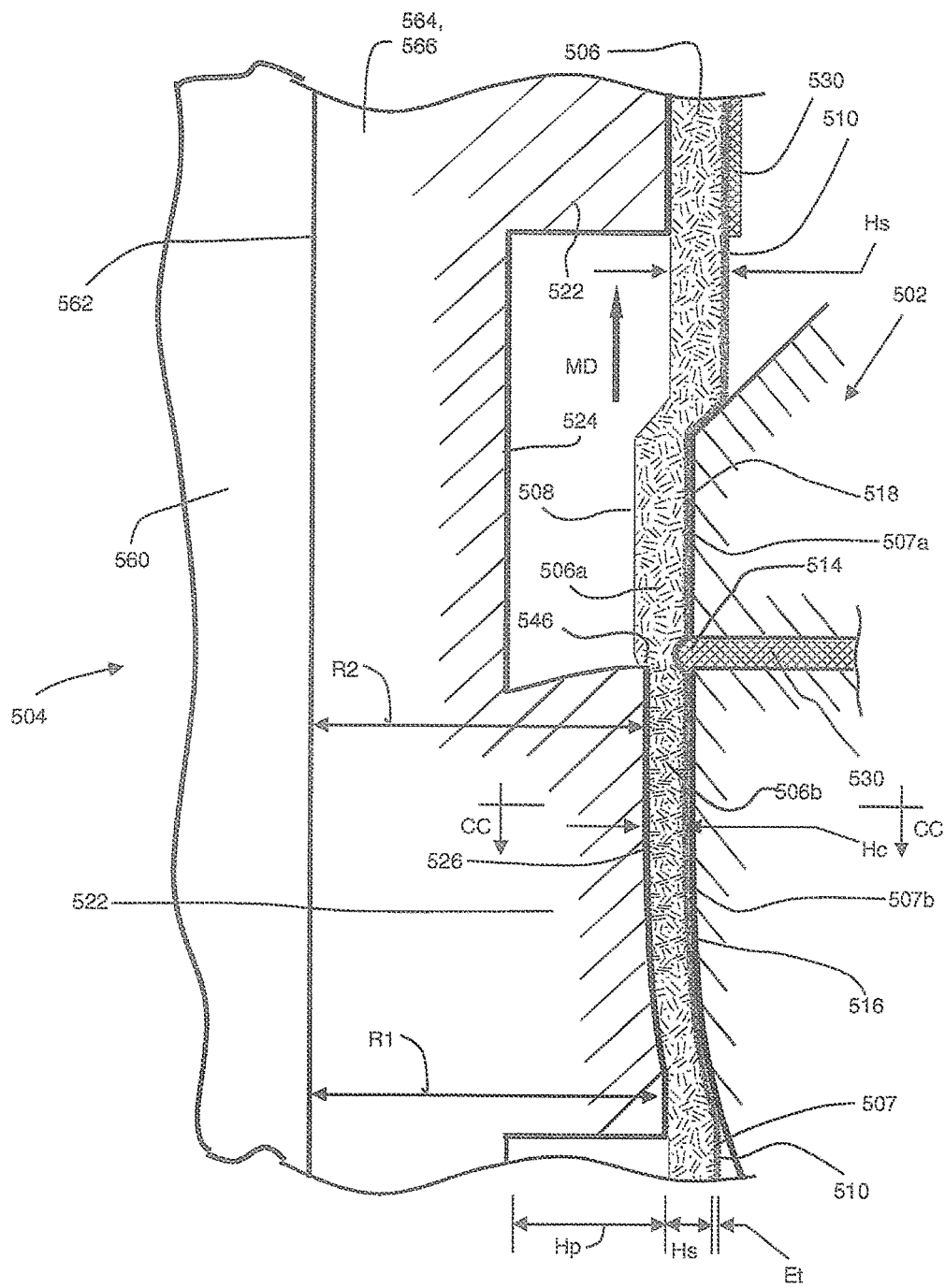
FIG. 9C is a detailed cross-sectional view of the substrate carrier, substrate, and elastic material of FIG. 9B wherein the base surface is advancing past the slot opening of the slot die applicator such that the substrate and elastic material are between the slot opening of the slot die applicator and a leading edge of an advancing pattern surface.

FIG. 9C is a detailed cross-sectional view of the substrate carrier 504, substrate 506, and elastic material 507 of FIG. 9B wherein the base surface 524 has advanced past the slot opening 514 of the slot die applicator 502 such that a portion 506b, 507b of the substrate 506 and elastic material 507 is between the first lip 516 of the slot die applicator 502 and a leading edge 546 of an advancing pattern surface 526. As previously discussed, the minimum distance, Hg, between the pattern surface 526 of the uncompressed pattern element 522 and the first lip 516 and the second lip 518 is less than the sum of the unconstrained caliper, Hs, of the substrate 506 and the maximum thickness, Et, of the elastic material 507. As such, a portion 506b, 507b of substrate 506 and the elastic material 507b between the pattern surface 526 and the first lip 516 is pressed against and exerts forces on the pattern surface 526. Thus, the pattern element 522 and/or base surface 524 compresses, allowing the pattern surface 526 to deflect away from the first lip 516 to define a minimum distance, R2, between the pattern surface 526 and the non-compliant support surface 562. The fluid 530 being discharged from the slot opening 514 is shown in FIG. 9C as beginning to transfer to the second surface 510 of the substrate and the elastic material 507 as the leading edge 546 of the pattern surface 526 and adjacent portion of the substrate 506 begin to advance past the slot opening 514.

With continued reference to FIG. 9C, the compression of the pattern element 522 and/or base surface 524 allows the pattern surface 526 to deflect away from the first lip 516 to define a compressed distance, Hc, between the pattern surface 526 and the first lip 516. When the substrate 506 is made from a material, such as a film, the substrate 506 may maintain a caliper that is substantially the same as the unconstrained caliper, Hs, while advancing between the pattern surface 526 and the first lip 516. Thus, the pattern surface 526 may deflect by a distance represented by the difference of Hg and the sum of Hs and Et, and in some instances, the distance R2, may be calculated as:

$$R2 = R1 + Hg - Hs - Et$$

In such a scenario, the compressed distance, Hc, may also be equal to or substantially equal to the sum of the unconstrained caliper, Hs, and the maximum thickness, Et, of the elastic material.

Still referring to FIG. 9C, when the substrate 506 is made from a material, such as a nonwoven or laminate including a nonwoven layer, the substrate 506 may be compressed to a caliper that is less than the unconstrained caliper, Hs, while advancing between the pattern surface 526 and the first lip 516. In such a scenario, the compressed distance, Hc, may be less than the sum of the unconstrained caliper, Hs, and the maximum thickness, Et, of the elastic material. In other words, the substrate 506 may be compressed to a caliper that is less than the compressed distance, Hc. Thus, the pattern surface 526 may deflect by a distance represented by the difference of Hg and Hc, and in some instances, the distance R2, may be calculated as:

$$R2=R1+Hg-Hc$$

In some instances, the elastic material 507 may define a cross directional width dimension that is less than the pattern surface 526. As such, pattern surface 526 may deflect by different distances when advancing past the slot die applicator 502. For example, FIG. 9CC1 shows a cross sectional view of the pattern element 522 of FIG. 9C wherein the pattern surface is deflected by different distances, wherein the elastic material 507 is in the form of an elastic strand 507a. As shown in FIG. 9CC1, the location where both the advancing elastic strand 507 and substrate 506 are between slot die applicator 502 and the pattern element 522, a first portion 526a of the pattern surface 526 is deflected away from the first lip 516 to define a minimum distance, R2, between the pattern surface 526 and the non-compliant support surface 562, wherein R2 may be calculated as described above. In addition, the location where only the advancing substrate 506 is between slot die applicator 502 and the pattern element 522, a second portion 526b of the pattern surface 526 is deflected away from the first lip 516 to define a distance, R3, between the pattern surface 526 and the non-compliant support surface 562, wherein R3 is greater than R2 and less than R1.

As such, when the substrate 506 is made from a material, such as a film, the substrate 506 may maintain a caliper that is substantially the same as the unconstrained caliper, Hs, while advancing between the pattern surface 526 and the first lip 516. Thus, the second portion 526b of the pattern surface 526 may deflect by a distance represented by the difference of Hg and Hs, and in some instances, the distance R3, may be calculated as:

$$R3=R1+Hg-Hs$$

With continued reference to FIG. 9CC1, when the substrate 506 is made from a material, such as a nonwoven or laminate including a nonwoven layer, the substrate 506 may be compressed to a caliper that is less than the unconstrained caliper, Hs, while advancing between the pattern surface 526 and the first lip 516. Thus, the second portion 526b of the pattern surface 526 may deflect by a distance represented by:

$$R3<R1+Hg-Hs$$

As previously mentioned, the elastic material 507 may be in various forms, such as for example, elastic strands, ribbons, and/or panels. For example, similar to FIG. 9CC1, FIG. 9CC2 shows a cross sectional view of the pattern element 522 of FIG. 9C wherein the pattern surface is deflected by different distances reflected by R2 and R3, wherein the elastic material 507 is in the form of an elastic ribbon 507b.

Figure 9D:
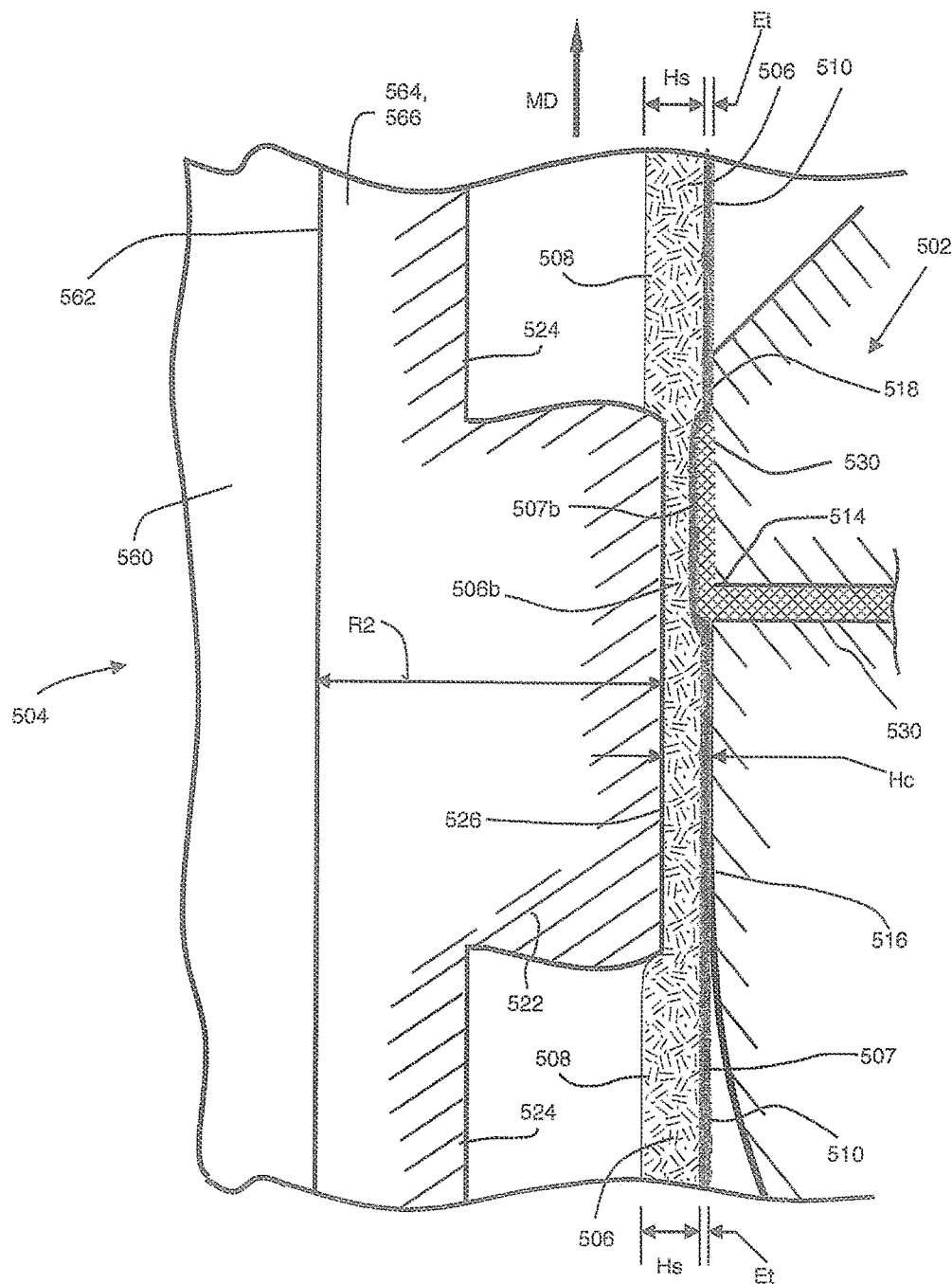
FIG. 9D is a detailed cross-sectional view of the substrate carrier, substrate, and elastic material of FIG. 9C wherein the base surface has advanced past the slot opening of the slot die applicator such that the substrate and elastic material are between the slot opening of the slot die applicator and an advancing pattern surface.

FIG. 9D is a detailed cross-sectional view of the substrate carrier 504 and substrate of FIG. 9C wherein the base surface 524 and leading edge 546 of the pattern surface 526 has advanced past the slot opening 514 of the slot die applicator 502 such that the portion 506b, 507b of the advancing substrate 506 and elastic material 507 is between the slot opening 514 of the slot die applicator 502 and an advancing pattern surface 526. Because the minimum distance, Hg, between the pattern surface 526 of the uncompressed pattern element 522 and the first lip 516 and the second lip 518 is less than the sum of the unconstrained caliper, Hs, of the substrate 506 and the maximum thickness, Et, of the elastic material 507, the portion 506b, 507b of substrate 506 and elastic material 507 between the pattern surface 526 and the first lip 516 and second lip 518 of the slot die applicator 502 presses against and exerts forces on the pattern surface 526. As such, the compliant pattern element 522 and/or base surface 524 are compressed, allowing the pattern surface 526 to deflect away from the first lip 516 and second lip 518, as discussed above with reference to the distance R2. The fluid 530 being discharged from the slot opening 514 is shown in FIG. 9D as being transferred to the second surface 510 of the substrate 506 and the elastic material 507 as the pattern surface 526 and adjacent portion 506b, 507b of the substrate 506 and the elastic material 507 advance past the slot opening 514.

Figure 9E:
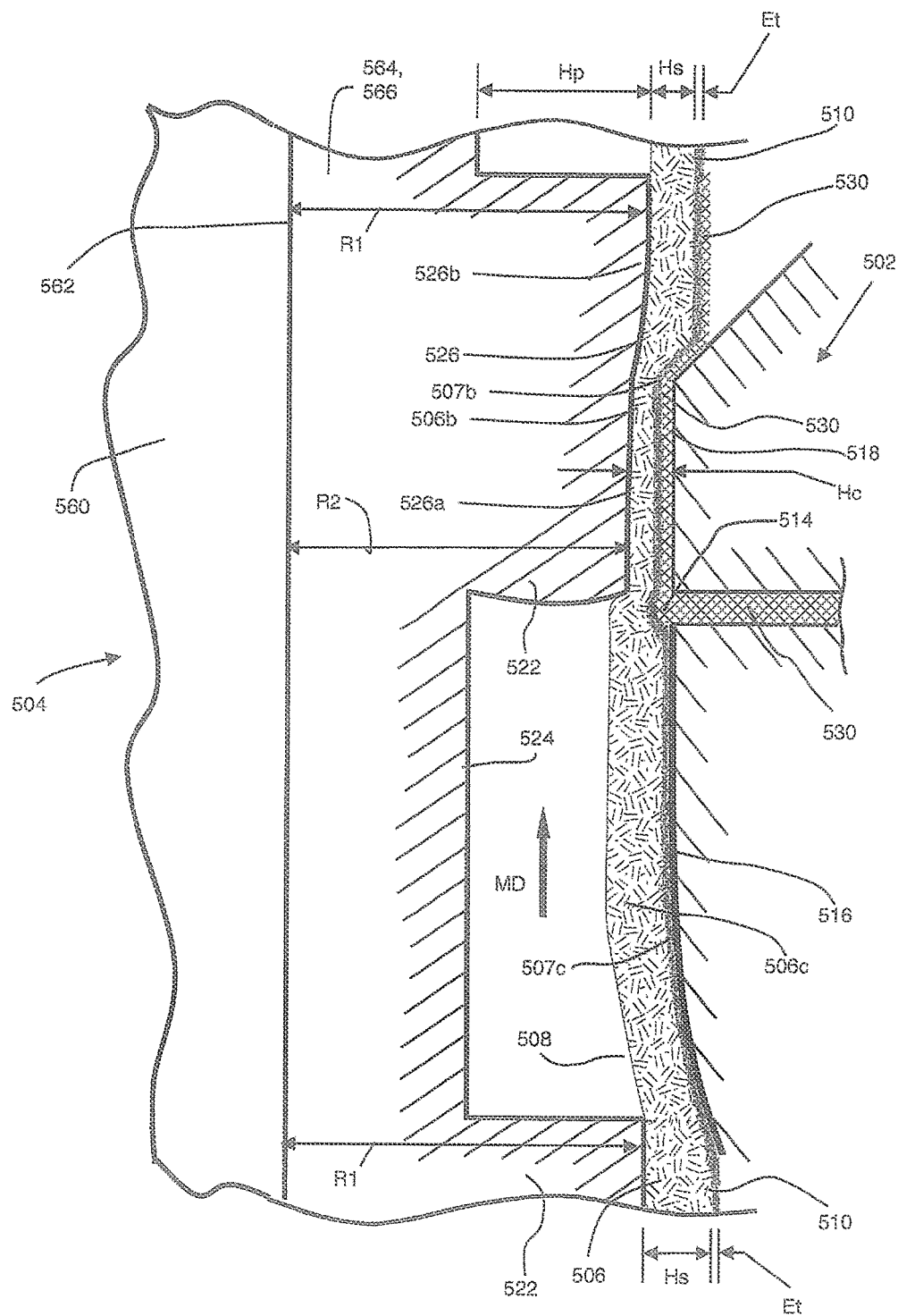
FIG. 9E is a detailed cross-sectional view of the substrate carrier and substrate of FIG. 9D wherein the pattern surface has advanced past the slot opening of the slot die applicator.

FIG. 9E is a detailed cross-sectional view of the substrate carrier 504, substrate 506, and elastic material 507 of FIG. 6D wherein the portion 506b, 507b of the substrate 506, the elastic material 507, and the pattern surface 526 have advanced past the slot opening 514 of the slot die applicator 502. As shown in FIG. 9E, an upstream portion 526a of the pattern surface 526 is adjacent the second lip 518, and a downstream portion 526b of the pattern surface 526 has advanced past the second lip 518. As such, the portion 506b, 507b of the advancing substrate 506 and elastic material 507 between the second lip 518 of the slot die applicator 502 and the upstream portion 526a of the advancing pattern surface 526 presses against and exerts forces on the pattern surface 526. As such, the compliant pattern element 522 and/or base surface 524 are compressed, allowing the upstream portion 526a of the pattern surface 526 to deflect away from the first lip 516 and second lip 518 to define the minimum distance, R2, between the upstream portion 526a of the pattern surface 526 and the non-compliant support surface 562.

With continued reference to FIG. 9E, the downstream portion 526b of the pattern surface 526 has advanced past the second lip 518 of the slot die applicator 502, and as such, the portion 506b, 507b of the substrate 506 and elastic material 507 is no longer pressing against downstream portion 526b of the pattern surface 526, allowing the compliant pattern element 522 and/or base surface 524 to return to an uncompressed state wherein the downstream portion 526b of the pattern surface 526 deflects back away from the non-compliant surface 562 such that the minimum distance between the non-compliant surface 562 and the downstream portion 526b pattern surface 526 is the distance, R1. Once the upstream portion 526a of the pattern surface 526 has also advanced past the second lip 518, the remainder of the compliant pattern element 522 and/or base surface 524 may return to an uncompressed state wherein the both the upstream portion 526a and downstream portion 526b of the pattern surface 526 have deflected away from the non-compliant surface 562 such that the minimum distance between the non-compliant surface 562 and the pattern surface 526 is the distance, R1.

Still referring to FIG. 9E, an uncompressed portion 506c, 507c of the advancing substrate 506 and the elastic material 507 is between the slot opening 514 of the slot die applicator 502 and an advancing base surface 524. Because the minimum distance, Hb, between the base surface 524 and the first lip 516 and the second lip 518 that is greater than the sum of the unconstrained caliper, Hs, of the substrate and the maximum thickness, Et, of the elastic material 507, a portion 506c, 507c of substrate 506 and elastic material 507 that advances between the base surface 524, slot opening 514, and the first lip 516 of the slot die applicator 502 is uncompressed. As such, the fluid 530 being discharged from the slot opening 514 is shown in FIG. 9E as ceasing to be transferred to the second surface 510 of the substrate 506 and the elastic material 507 as the base surface 524 and adjacent uncompressed portion 506c, 507c of the substrate 506 and elastic material 507 advance past the slot opening 514.

Figure 10:
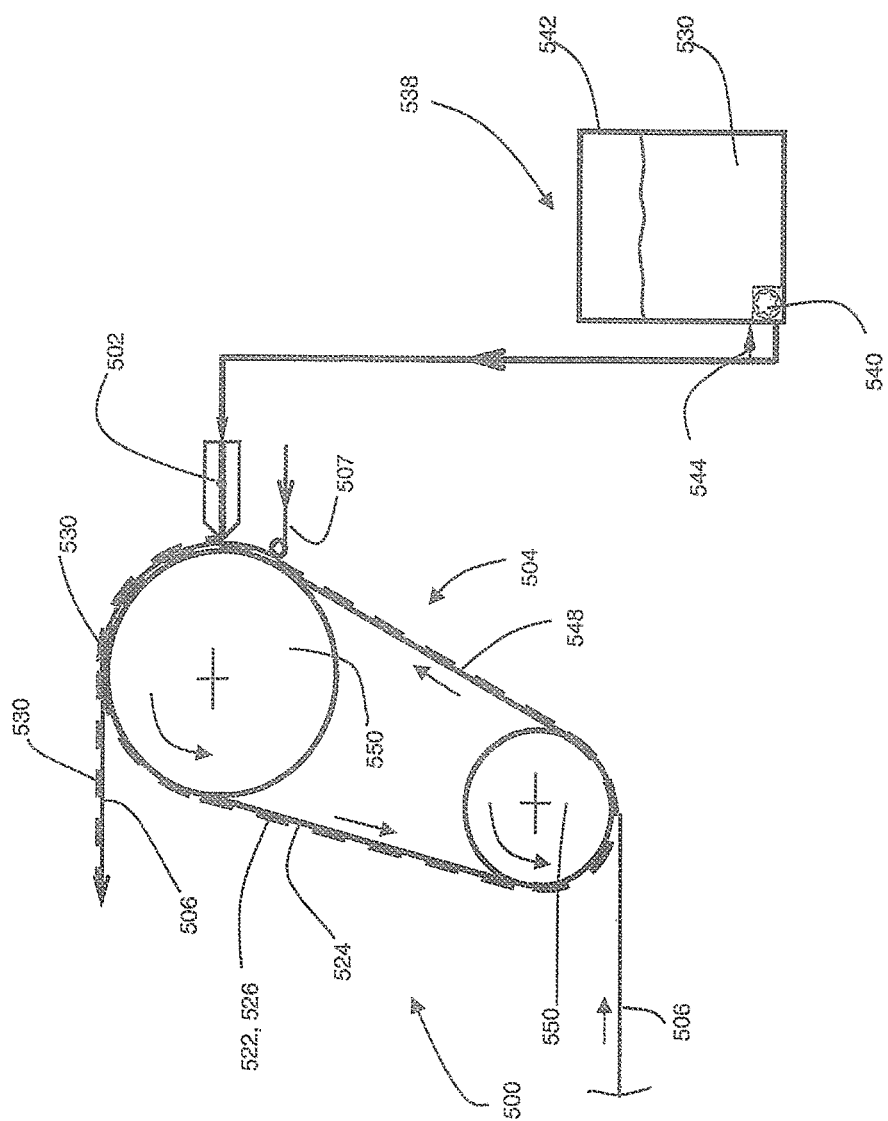
FIG. 10 is a schematic cross-sectional side view of an embodiment of a fluid application apparatus with a substrate carrier including a pattern belt.
Figure 11:
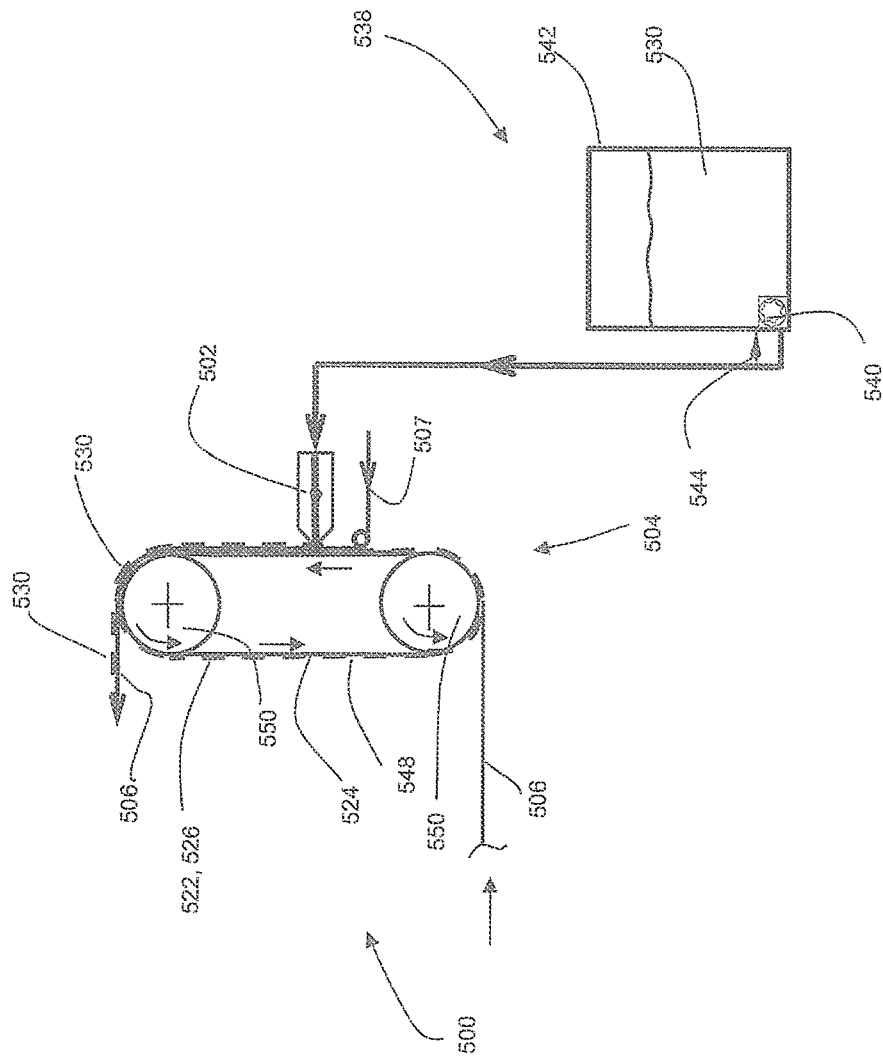
FIG. 11 is a schematic cross-sectional side view of another embodiment of a fluid application apparatus with a substrate carrier including a pattern belt.
Figure 12:
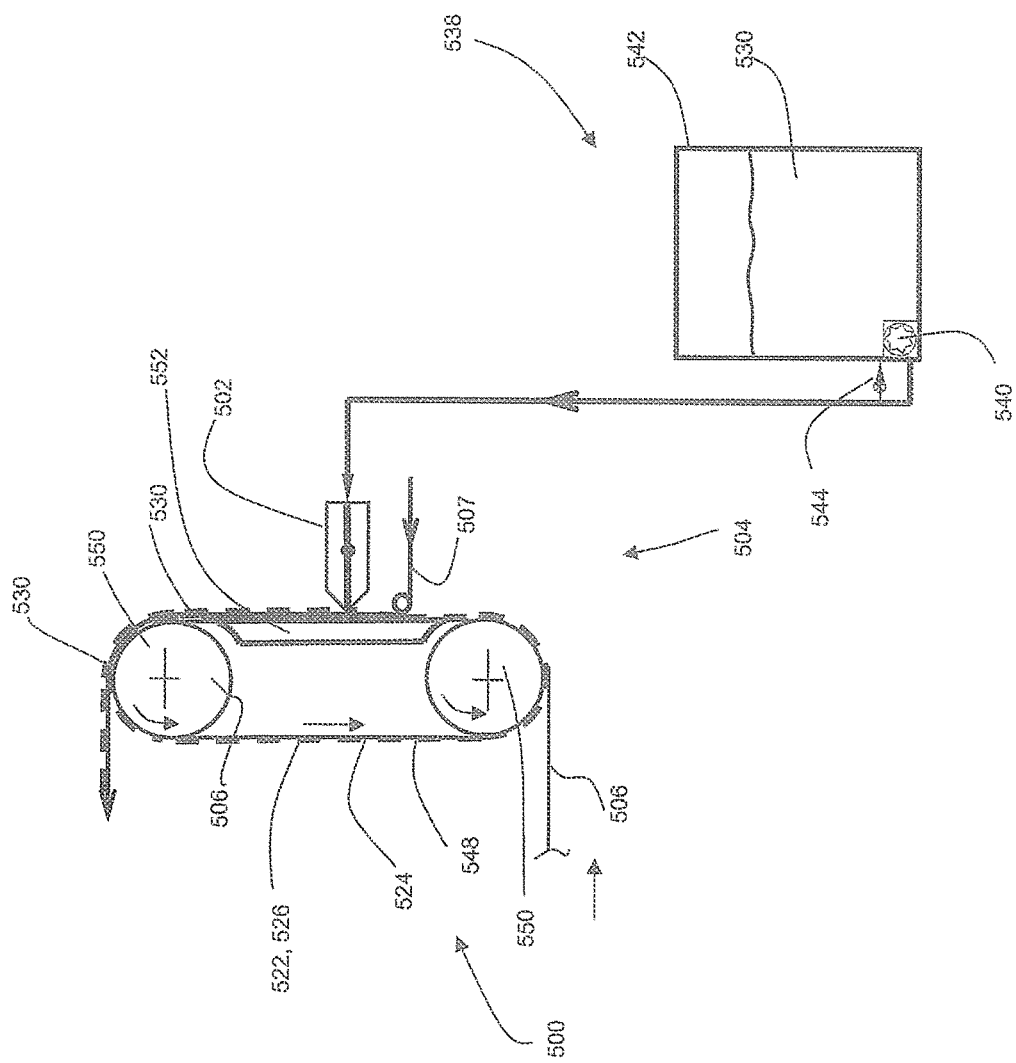
FIG. 12 is a schematic cross-sectional side view of another embodiment of a fluid application apparatus with a substrate carrier including a pattern belt and a backup plate.

As previously mentioned, various forms and configurations of substrate carriers may be used with the presently disclosed methods and apparatuses. For example, FIG. 10 shows a schematic cross-sectional side view of an embodiment of a fluid application apparatus 500 with a substrate carrier 504 including an endless pattern belt 548. The pattern belt 548 is wrapped around two rollers 550 adapted to advance pattern belt 548 and substrate past the slot die applicator 502. The pattern belt 548 may include various different combinations, shapes, and types of pattern elements 522 and base surfaces 524 and/or holes 536 as previous described. As shown in FIG. 10, the slot die applicator 502 is adjacent the pattern belt 548 at a location where the pattern belt 548 is partially wrapped around one of the rollers 550. It is to be appreciated that the slot die applicator 502 may be located adjacent to other locations of the pattern belt 548. For example, FIG. 11 shows a schematic cross-sectional side view of an embodiment of a fluid application apparatus 500 wherein the slot die applicator 502 is adjacent the pattern belt 548 at a location between the rollers 550. And FIG. 12 shows a schematic cross-sectional side view of the embodiment of FIG. 8 with a backup plate 552 located behind the pattern belt 548, wherein the backup plate 548 provides support to the pattern belt 548 to help prevent the pattern belt from deflecting away from the slot die applicator 502.

With reference to the above description and associated figures, it is to be appreciated that the apparatuses 500 herein may be used to apply adhesive 530 discharged from a slot die applicator 502 to a substrate 506 and elastic material 507 in a pattern by continuously advancing the substrate and elastic material 507 in a machine direction past a first lip 516, second lip 518, and slot opening 514 in the slot die applicator 502. The substrate 506 may be engaged with a substrate carrier 504 that may include a base surface 524 and a pattern element 522, wherein the pattern element includes a pattern surface 526. The pattern element 522 protrudes from the base surface 524 to define a distance, Hp, between the pattern surface 526 and the base surface 524. As previously mentioned, in some embodiments, the substrate carrier may include holes 536 instead of or in combination with base surfaces 526 adjacent the pattern element 522. The substrate carrier 504 is positioned adjacent the slot die applicator 502 to define a minimum distance, Hg, between the pattern surface 526 of the uncompressed pattern element 522 and the first lip 516 and the second lip 518 that is less than the sum of the unconstrained caliper, Hs, of the substrate 506 and the maximum thickness, Et, of the elastic material 507. The second surface 510 of the substrate 506 and elastic material 507 may be advanced past the slot die applicator 502 while the first surface 508 of the substrate 506 is disposed on the substrate carrier 504. And the substrate 506 and elastic material 507 are intermittently compressed between the slot die applicator 502 and the pattern surface 526 of the pattern element 522 by advancing the pattern element as the pattern surface of the pattern element advances past the first lip 516, the slot opening 514, and the second lip 518 of the slot die applicator 502 while the first surface 508 of the substrate 506 is disposed on the substrate carrier 504.

It is to be appreciated that the methods and apparatuses herein may deposit fluids, such as adhesives, onto advancing a substrate advancing in a machine direction MD in various designs or patterns. In the context of the previous discussion, the apparatuses and methods herein may be used to provide for the application adhesives in patterns to substrates and components during the manufacture of an absorbent article. For example, adhesives may be applied in various patterns to portions of any of the topsheet, backsheet films, backsheet nonwovens, absorbent core, core encapsulation webs, acquisition layer, surge layer, secondary topsheet layer, leg cuffs, waist feature, ears, and fastening elements during the manufacture of an absorbent article. In some instances, the adhesive may be a different color than that of the substrate. In some applications, the apparatuses and methods herein may be adapted to apply adhesives in absorbent core assembly processes, such as described for example in U.S. Patent Publication Nos. US2006/0021695A1; US2006/0048880A1; US2008/0215166A1; and US2010/0051166A1. In some instances, the apparatuses and methods herein may be configured to apply fluid formulations in the form of wetness indicators, such as disclosed for example in U.S. Patent Publication No. US2011/0137274A1. In yet other instances, the apparatuses and methods herein may be configured to apply fastening adhesives for feminine care articles, including sanitary napkins, panty liners, adult incontinence pads, and the like, such as disclosed for example in European Patent Publication No. EP0745368A1.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for applying adhesive discharged from a slot die applicator to a substrate and an elastic material, the slot die applicator including a slot opening, a first lip, and a second lip, the slot opening located between the first lip and the second lip; wherein the substrate has a first surface disposed opposite of a second surface and an unconstrained caliper, Hs, and wherein the elastic material has a maximum thickness, Et, the method comprising the steps of:
  advancing the substrate in a machine direction;
  advancing the elastic material in the machine direction;
  positioning the elastic material on the second surface of the substrate;
  engaging the substrate with a substrate carrier, the substrate carrier comprising: a non-compliant support surface and a pattern element, the pattern element including a pattern surface, the substrate carrier positioned adjacent the slot die applicator to define a minimum distance, Hg, between the pattern surface of the pattern element and the first lip and the second lip of the slot die applicator that is less than the sum of the unconstrained caliper, Hs, of the substrate and the maximum thickness, Et, of the elastic material;
  advancing the second surface of the substrate and the elastic material past the slot die applicator while the first surface of the substrate is disposed on the substrate carrier;
  intermittently deflecting a first portion of the pattern surface toward the non-compliant support surface by advancing the substrate and the elastic material between the pattern element and the first lip, the slot opening, and the second lip of the slot die applicator while the first surface of the substrate is disposed on the substrate carrier; and
  discharging adhesive from the slot opening of the slot die applicator onto the elastic material and the second surface of the substrate.

2. The method of claim 1, wherein the pattern element extends away from the non-compliant support surface to define a first minimum distance, R1, between the pattern surface and the non-compliant support surface, and wherein the step of intermittently deflecting further comprises defining a second minimum distance, R2, between the pattern surface and the non-compliant surface, wherein R2 is less than R1.

3. The method of claim 2, further comprising the step of: intermittently deflecting a second portion of the pattern surface toward the non-compliant support surface such to define a third minimum distance, R3, between the pattern surface and the non-compliant surface, wherein R3 is less than R1, and wherein R3 is greater than R2, by advancing the substrate between the pattern element and the first lip, the slot opening, and the second lip of the slot die applicator while the first surface of the substrate is disposed on the substrate carrier.

4. The method of claim 1, wherein the minimum distance, Hg, between the pattern surface of the pattern element and the first lip and the second lip of the slot die applicator is less than the unconstrained caliper, Hs, of the substrate.

5. The method of claim 1, wherein the substrate carrier comprises a roller.

6. The method of claim 1, wherein the elastic material comprises an elastic strand.

7. The method of claim 1, wherein the elastic material comprises an elastic ribbon.

8. The method of claim 1, wherein the substrate comprises a nonwoven.

9. The method of claim 1, wherein the substrate comprises a nonwoven layer and a film layer.

10. A method for applying adhesive discharged from a slot die applicator to a substrate and an elastic material, the slot die applicator including a slot opening, a first lip, and a second lip, the slot opening located between the first lip and the second lip of the slot die applicator; wherein the substrate has a first surface disposed opposite of a second surface and an unconstrained caliper, Hs, and wherein the elastic material has a maximum thickness, Et, the method comprising the steps of:
  advancing the substrate in a machine direction;
  advancing the elastic material in the machine direction;
  positioning the elastic material on the second surface of the substrate;
  engaging the substrate with a substrate carrier, the substrate carrier comprising: a pattern element including a pattern surface, the substrate carrier positioned adjacent the slot die applicator to define a minimum distance, Hg, between the pattern surface of the pattern element and the first lip and the second lip that is less than the sum of the unconstrained caliper, Hs, of the substrate and the maximum thickness, Et, of the elastic material;
  advancing the second surface of the substrate and the elastic material past the slot die applicator while the first surface of the substrate is disposed on the substrate carrier;
  intermittently deflecting a first portion of the pattern surface away from the slot die applicator by advancing the substrate and the elastic material between the pattern element and the first lip, the slot opening, and the second lip of the slot die applicator while the first surface of the substrate is disposed on the substrate carrier; and
  discharging adhesive from the slot opening of the slot die applicator onto the elastic material and the second surface of the substrate.

11. The method of claim 10, wherein the minimum distance, Hg, between the pattern surface of the pattern element and the first lip and the second lip of the slot die applicator is less than the unconstrained caliper, Hs, of the substrate.

12. The method of claim 10, wherein the substrate carrier comprises a roller.

13. The method of claim 10, wherein the substrate carrier comprises an endless belt.

14. The method of claim 10, wherein the elastic material comprises an elastic strand.

15. The method of claim 10, wherein the elastic material comprises an elastic ribbon.

16. The method of claim 10, wherein the substrate comprises a nonwoven.

17. The method of claim 10, wherein the substrate comprises a nonwoven layer and a film layer.

18. A method for making an elastic laminate, the method comprising the steps of:
  advancing a substrate, the substrate comprising a first surface disposed opposite of a second surface;
  positioning the elastic material on the second surface of the substrate;
  engaging the substrate with a substrate carrier, the substrate carrier comprising: a pattern element including a pattern surface, the substrate carrier positioned adjacent the slot die applicator to define a minimum distance, Hg, between the pattern surface of the pattern element and the first lip and the second lip of the slot die applicator that is less than the sum of the unconstrained caliper, Hs, of the substrate and the maximum thickness, Et, of the elastic material;
  advancing the second surface of the substrate and the elastic material past the slot die applicator while the first surface of the substrate is disposed on the substrate carrier;
  intermittently deflecting a first portion of the pattern surface away from the slot die applicator by advancing the substrate and the elastic material between the pattern element and the first lip, the slot opening, and the second lip of the slot die applicator while the first surface of the substrate is disposed on the substrate carrier; and discharging adhesive from the slot opening of the slot die applicator onto the elastic material and the second surface of the substrate.

19. The method of claim 18, further comprising the step of: folding a first portion of the second surface the substrate onto the elastic material.

20. The method of claim 18, further comprising the step of: adhering a second substrate with the second surface of the substrate and the elastic material.

* * * * *